United States Patent
Hoener et al.

(10) Patent No.: US 10,005,736 B1
(45) Date of Patent: Jun. 26, 2018

(54) PYRIDINE AND PYRIMIDINE DERIVATIVES

(71) Applicant: Hoffmann-La Roche Inc., Little Falls, NJ (US)

(72) Inventors: Marius Hoener, Basel (CH); Juergen Wichmann, Basel (CH)

(73) Assignee: Hoffman-La Roche Inc., Little Falls, NJ (US)

( * ) Notice: Subject to any disclaimer, the term of this patent is extended or adjusted under 35 U.S.C. 154(b) by 0 days. days.

(21) Appl. No.: 15/891,922

(22) Filed: Feb. 8, 2018

Related U.S. Application Data

(63) Continuation of application No. PCT/EP2016/068919, filed on Aug. 9, 2016.

(30) Foreign Application Priority Data

Aug. 12, 2015 (EP) .................................... 15180759

(51) Int. Cl.
*C07D 239/24* (2006.01)
*C07D 211/80* (2006.01)
*C07D 333/20* (2006.01)
*A61P 25/18* (2006.01)

(52) U.S. Cl.
CPC ............ *C07D 239/24* (2013.01); *A61P 25/18* (2018.01); *C07D 211/80* (2013.01); *C07D 333/20* (2013.01)

(58) Field of Classification Search
CPC .. C07D 239/24; C07D 211/80; C07D 333/20; A61P 25/18
USPC ................................... 514/212.07
See application file for complete search history.

(56) References Cited

FOREIGN PATENT DOCUMENTS

WO 2010/033168 A2 3/2010

OTHER PUBLICATIONS

Bridges Richard J. et al., "The excitatory amino acid transporters: pharmacological insights on substrate and inhibitor specificity of the EAAT subtypes" Pharmacology & Therapeutics 107(3):271-285 (Sep. 1, 2005).
ISR for PCT/EP2016/068919 (Oct. 4, 2016).

*Primary Examiner* — Kristin A Vajda
(74) *Attorney, Agent, or Firm* — Brian L. Buckwalter

(57) ABSTRACT

The present invention relates to compounds of formula I

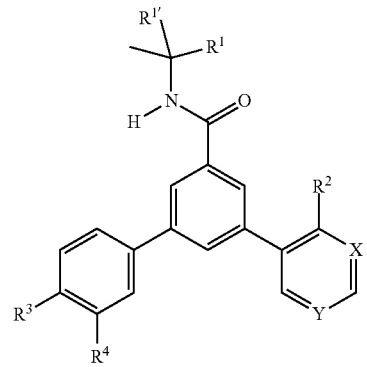

wherein
$R^{1'}$ is $CH_3$
$R^1$ is methyl, ethyl, $CF_3$, $CH_2OH$, cyclopropyl or cyano, or $R^{1'}$ and $R^1$ may form together a 1,1-dioxo-tetrahydro-thiophen-3-yl ring;
$R^2$ is hydrogen, methyl, ethyl, isopropyl, tert-butyl or cyclopropyl;
$R^3$ is Cl, F, $CF_3$, cyano, methyl, methoxy or cyclopropyl;
$R^4$ is hydrogen, methyl or F;
X is N or CH;
Y is N or CH;
with the proviso that X and Y are not simultaneously CH; or to a pharmaceutically acceptable salt or acid addition salt, to a racemic mixture, or to its corresponding enantiomer and/or optical isomer and/or stereoisomer thereof.
The compounds of formula I may be used in the treatment of psychiatric disorders such as schizophrenia, bipolar disorder, obsessive-compulsive disorder or autism spectrum disorder.

22 Claims, No Drawings

PYRIDINE AND PYRIMIDINE DERIVATIVES

CROSS REFERENCE TO RELATED APPLICATIONS

This application is a continuation of International Application No. PCT/EP2016/068919 having an international filing date of Aug. 9, 2016 and which claims benefit under 35 U.S.C. § 119 to European Patent Application No. 15180759.1 having an international filing date of Aug. 12, 2015. The entire contents of both are incorporated herein by reference.

FIELD OF THE INVENTION

The present invention relates to organic of general formula I that inhibit EAAT3 (excitatory amino acid transporter 3) inhibitors. The compounds of formula I may be used in the treatment of psychiatric disorders such as schizophrenia, bipolar disorder, obsessive-compulsive disorder or autism spectrum disorder.

BACKGROUND OF THE INVENTION

The excitatory amino acid transporter 3 (EAAT3), also referred to in human studies as solute carrier family 1, member 1 (systematic gene name: SLC1A1) and in rodents as excitatory amino acid carrier 1 (EAAC1), is a high-affinity anionic amino acid transporter found in neurons throughout the cortex and in the hippocampus, basal ganglia (striatum, thalamus), and the olfactory bulb. EAAT3 functions to buffer local glutamate concentrations at excitatory synapses, for example in the hippocampus, and modulates the differential recruitment of glutamate receptor subtypes at extrasynaptic sites. Furthermore, EAAT3 is thought to be involved in facilitating GABA and glutathione biosynthesis. EAAT3 is a member of the EAAT family that mediates the uptake of glutamate into neuronal and glial cells of the mammalian CNS. Two transporters expressed primarily in glia, EAAT1 and EAAT2, are crucial for glutamate homeostasis in the adult mammalian brain and for rapid clearance of glutamate from the synaptic cleft. Three neuronal transporters (EAAT3, EAAT4, and EAAT5) appear to have additional functions in regulating and processing cellular excitability with EAAT3 being abundantly expressed throughout the CNS (EAAT4 is unique to Purkinje cells of the cerebellum and EAAT5 is expressed in rod photoreceptor and bipolar cells of the retina).

EAATs are assembled as trimers, and the existence of multiple isoforms raises the question of whether certain isoforms can form hetero-oligomers. In the mammalian brain, the specificity of excitatory synaptic transmission depends on rapid diffusion of glutamate away from active synapses and the powerful uptake capacity of glutamate transporters in astrocytes. The extent to which neuronal glutamate transporters influence the lifetime of glutamate in the extracellular space remains unclear, but it is thought to be minor. EAAT3, the predominant neuronal glutamate transporter at excitatory synapses in hippocampal area CA1, buffers glutamate released during synaptic events and prolongs the time course of its clearance by astrocytes. EAAT3 does not significantly alter activation of receptors in thesynaptic cleft. Instead, it reduces recruitment of perisynaptic/extrasynaptic NR2B-containing NMDARs, thereby facilitating induction of long-term potentiation by short bursts of high-frequency stimulation. Specific EAAT3 inhibitors may have the potential to locally and specifically strengthen particular synapses.

Obsessive-compulsive disorder (OCD) is among the most common mental disorders (prevalence 1-3%), and is at least as prevalent as schizophrenia and bipolar disorder. In the United States, one in 50 adults suffers from OCD. OCD affects children and adolescents as well as adults. Roughly one third to one half of adults with OCD reports a childhood onset of the disorder, and the disorder is typically chronic in nature. Treatment consists of predominantly serotonergic TCAs (clomipramine) or SSRIs in combination with cognitive-behavioral therapy (CBT). Overall, response to these interventions is of some but still limited benefit (approximately comparable to antidepressant response in MDD), and given the chronicity of OCD, the unmet medical need remains very high. OCD has been linked to serotonin and glutamate abnormalities. The hypothesis of glutamate signaling dysfunction in OCD is based on findings from neuroimaging, animal models, positional cloning and treatment studies The obsessive-compulsive symptomatology in OCD has considerable phenomenological, epidemiological and possibly (aetio)-pathophysiological overlap with a core autism spectrum disorder criterion: "restricted, repetitive patterns of behavior, interests, or activities" (taken from proposed DSM-5 revision). In support of this notion, human genetics studies have linked both the serotonin transporter and EAAT3 (SLC1A1) genes to autism spectrum disorder (ASD) or rigid-compulsive behavior in ASD and to OCD.

In addition, obsessive-compulsive symptoms induced by antipsychotics in schizophrenic bipolar disorder patients have been linked to EAAT3 (SLC1A1) gene variants. Postmortem brain studies have shown that both classic and atypical antipsychotics reduce EAAT3, suggesting an involvement of this transporter in neuroleptic mechanisms beyond dopamine and serotonin modulation. Moreover, genetic variation in the human gene EAAT3 (SLC1A1) has been associated with antipsychotic drug response.

There is converging evidence from neurobiological data, human genetics, imaging studies and experimental treatments that EAAT3 is a key pathophysiological element in OCD and rigid-compulsive behavior in autism and in schizophrenia. (A. A. Jensen et al., Curr. Opin. Pharmacol. 2015 20:116-123; L. A. Jarzylo and H-Y. Man, J. Neurosci., 2012 32(7):2552-2563; A. Scimemi et al., J. Neurosci 2009 29(46):14581-14595; J. R. Wendland et al., Arch. Gen. Psychiatry, 2009 66(4):408-416; R. Bridges and C. S. Esslinger, Pharmacol. Ther. 2005 107(3):271-285; A. Nieoullon et al., J. Neurochem. 2006 98(4):1007-1018; K. Aoyama et al. Nat. Neurosci., 2006 9:119-126).

BRIEF SUMMARY OF THE INVENTION

The present invention relates to compounds of formula I

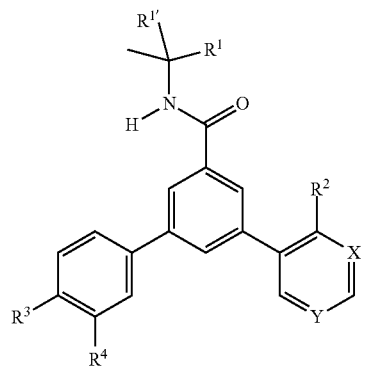

wherein

R$^{1'}$ is methyl;

R$^1$ is methyl, ethyl, CF$_3$, CH$_2$OH, cyclopropyl or cyano; or
R$^{1'}$ and R$^1$ may form together a 1,1-dioxo-tetrahydro-thiophen-3-yl ring;

R$^2$ is hydrogen, methyl, ethyl, isopropyl, tert-butyl or cyclopropyl;

R$^3$ is Cl, F, CF$_3$, cyano, methyl, methoxy or cyclopropyl;

R$^4$ is hydrogen, methyl or F;

X is N or CH;

Y is N or CH;

with the proviso that X and Y are not simultaneously CH;

or to a pharmaceutically acceptable salt or acid addition salt, to a racemic mixture, or to its corresponding enantiomer, or mixture of enantiomers, and/or optical isomer and/or stereoisomer thereof.

The compounds of formula I may be used in the treatment of psychiatric disorders such as schizophrenia, bipolar disorder, obsessive-compulsive disorder or autism spectrum disorder.

DETAILED DESCRIPTION OF THE INVENTION

It has been surprisingly been found that the compounds of general formula I are EAAT3 inhibitors.

Compounds of formula I are distinguished by having valuable therapeutic properties. They can be used in the treatment or prevention of disorders, relating to EAAT3 inhibitors. The most preferred indications for compounds which are EAAT3 inhibitors are psychiatric disorders such as schizophrenia, bipolar disorder, obsessive-compulsive disorder or autism spectrum disorder.

The present invention relates to compounds of formula I and to their pharmaceutically acceptable salts, to their use in the treatment of psychiatric disorders such as schizophrenia, bipolar disorder, obsessive-compulsive disorder or autism spectrum disorder, to compounds of formulas I, IA, IB, IC, ID, IE, IF and IG as pharmaceutically active substances, to the processes for their production as well as to their use in the treatment or prevention of disorders, relating to EAAT3 inhibitors, such as schizophrenia, bipolar disorder, obsessive-compulsive disorder or autism spectrum disorder and to pharmaceutical compositions containing the compounds of formula IA A further object of the present invention is a method for the treatment or prophylaxis of psychiatric disorder such as schizophrenia, bipolar disorder, obsessive-compulsive disorder or autism spectrum disorder, which method comprises administering an effective amount of a compound of formula I to a mammal in need.

Furthermore, the invention includes all racemic mixtures, all their corresponding enantiomers and/or optical isomers, or analogues containing isotopes of hydrogen, fluorine, carbon, oxygen or nitrogen.

One object of the present invention are novel compounds of formula IA,

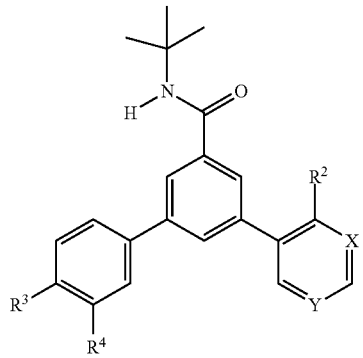

wherein

R$^2$ is hydrogen, methyl, ethyl, isopropyl, tert-butyl or cyclopropyl;

R$^3$ is Cl, F, CF$_3$, cyano, methyl, methoxy or cyclopropyl;

R$^4$ is hydrogen, methyl or F;

X is N or CH;

Y is N or CH;

with the proviso that X and Y are not simultaneously CH;

or a pharmaceutically acceptable salt or acid addition salt, a racemic mixture, or its corresponding enantiomer, or mixture of enantiomers, and/or optical isomer and/or stereoisomer thereof, for example the following compounds:

N-tert-Butyl-3-(4-chlorophenyl)-5-(4-methylpyridin-3-yl)-benzamide

N-tert-Butyl-3-(4-chlorophenyl)-5-pyridin-3-ylbenzamide

N-tert-Butyl-3-(4-chlorophenyl)-5-(4-propan-2-ylpyridin-3-yl)-benzamide

N-tert-Butyl-3-(4-chlorophenyl)-5-pyrimidin-5-ylbenzamide

N-tert-Butyl-3-(4-chlorophenyl)-5-(4-propan-2-ylpyrimidin-5-yl)-benzamide

N-tert-Butyl-3-(4-chlorophenyl)-5-(2-propan-2-ylpyridin-3-yl)-benzamide

N-tert-Butyl-3-(4-fluorophenyl)-5-(4-propan-2-ylpyrimidin-5-yl)-benzamide

N-tert-Butyl-3-(4-fluorophenyl)-5-(4-methylpyridin-3-yl)-benzamide

N-tert-Butyl-3-(4-fluorophenyl)-5-(2-methylpyridin-3-yl)-benzamide

N-tert-Butyl-3-(4-methylphenyl)-5-(4-propan-2-ylpyrimidin-5-yl)-benzamide

N-tert-Butyl-3-(3,4-difluorophenyl)-5-(4-propan-2-ylpyrimidin-5-yl)-benzamide

N-tert-Butyl-3-(4-cyclopropylphenyl)-5-(4-propan-2-ylpyrimidin-5-yl)-benzamide

N-tert-Butyl-3-(4-propan-2-ylpyrimidin-5-yl)-5-[4-(trifluoromethyl)-phenyl]-benzamide N-tert-Butyl-3-(4-fluoro-3-methylphenyl)-5-(4-propan-2-ylpyrimidin-5-yl)-benzamide N-tert-Butyl-3-(3-fluoro-4-methylphenyl)-5-(4-propan-2-ylpyrimidin-5-yl)-benzamide N-tert-Butyl-3-(4-chloro-3-fluorophenyl)-5-(4-propan-2-ylpyrimidin-5-yl)-benzamide N-tert-Butyl-3-(4-cyanophenyl)-5-(4-propan-2-ylpyrimidin-5-yl)-benzamide N-tert-Butyl-3-(4-methoxyphenyl)-5-(4-propan-2-ylpyrimidin-5-yl)-benzamide N-tert-Butyl-3-(4-chlorophenyl)-5-(4-cyclopropyl-pyrimidin-5-yl)-benzamide N-tert-Butyl-3-(4-chlorophenyl)-5-(4-ethyl-pyrimidin-5-yl)-benzamide N-tert-Butyl-3-(4-chlorophenyl)-5-(4-methyl-pyrimidin-5-yl)-benzamide or N-tert-Butyl-3-(4-tert-butyl-pyrimidin-5-yl)-5-(4-chlorophenyl)-benzamide.

One further object of the present invention are novel compounds of formula IB,

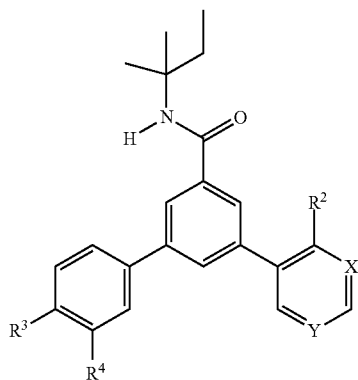

IB wherein
$R^2$ is hydrogen, methyl, ethyl, isopropyl, tert-butyl or cyclopropyl;
$R^3$ is Cl, F, $CF_3$, cyano, methyl, methoxy or cyclopropyl;
$R^4$ is hydrogen, methyl or F;
X is N or CH;
Y is N or CH;
with the proviso that X and Y are not simultaneously CH;
or a pharmaceutically acceptable salt or acid addition salt, a racemic mixture, or its corresponding enantiomer, or mixture of enantiomers, and/or optical isomer and/or stereoisomer thereof, for example the following compounds:

N-(2-Methylbutan-2-yl)-3-(4-methylphenyl)-5-pyridin-3-ylbenzamide

N-(2-Methylbutan-2-yl)-3-(4-methylphenyl)-5-pyrimidin-5-ylbenzamide

N-(2-Methylbutan-2-yl)-3-(4-methylphenyl)-5-(4-propan-2-ylpyrimidin-5-yl)-benzamide N-(2-Methylbutan-2-yl)-3-(4-methylphenyl)-5-(4-methyl-pyridin-3-yl)-benzamide N-(2-Methylbutan-2-yl)-3-(4-methylphenyl)-5-(2-methyl-pyridin-3-yl)-benzamide N-(2-Methylbutan-2-yl)-3-(4-methylphenyl)-5-(4-propan-2-ylpyridin-3-yl)-benzamide or N-(2-Methylbutan-2-yl)-3-(4-methylphenyl)-5-(2-propan-2-ylpyridin-3-yl)-benzamide.

One object of the present invention are novel compounds of formula IC,

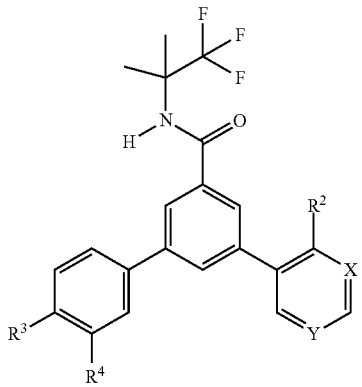

IC wherein
$R^2$ is hydrogen, methyl, ethyl, isopropyl, tert-butyl or cyclopropyl;
$R^3$ is Cl, F, $CF_3$, cyano, methyl, methoxy or cyclopropyl;
$R^4$ is hydrogen, methyl or F;
X is N or CH;
Y is N or CH;
with the proviso that X and Y are not simultaneously CH;
or a pharmaceutically acceptable salt or acid addition salt, a racemic mixture, or its corresponding enantiomer, or mixture of enantiomers, and/or optical isomer and/or stereoisomer thereof, for example the following compounds:

3-(4-Chlorophenyl)-5-(4-propan-2-ylpyrimidin-5-yl)-N-(1,1,1-trifluoro-2-methylpropan-2-yl)-benzamide or 3-(4-Chlorophenyl)-5-(2-methylpyridin-3-yl)-N-(1,1,1-trifluoro-2-methylpropan-2-yl)-benzamide.

One further object of the present invention are novel compounds of formula ID,

ID wherein
$R^2$ is hydrogen, methyl, ethyl, isopropyl, tert-butyl or cyclopropyl;
$R^3$ is Cl, F, $CF_3$, cyano, methyl, methoxy or cyclopropyl;
$R^4$ is hydrogen, methyl or F;
X is N or CH;
Y is N or CH;
with the proviso that X and Y are not simultaneously CH;
or a pharmaceutically acceptable salt or acid addition salt, a racemic mixture, or its corresponding enantiomer, or mixture of enantiomers, and/or optical isomer and/or stereoisomer thereof, for example the following compounds:

3-(4-Chlorophenyl)-N-(1-hydroxy-2-methylpropan-2-yl)-5-(4-propan-2-yl-pyrimidin-5-yl)-benzamide 3-(4-Fluorophenyl)-N-(1-hydroxy-2-methylpropan-2-yl)-5-(4-propan-2-yl-pyrimidin-5-yl)-benzamide or N-(1-Hydroxy-2-methylpropan-2-yl)-3-(4-propan-2-yl-pyrimidin-5-yl)-5-[4-(trifluoromethyl)-phenyl]-benzamide.

One object of the present invention are novel compounds of formula IE,

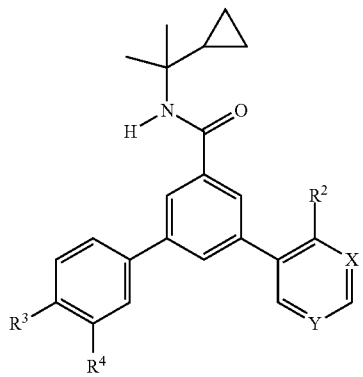

IE wherein
R² is hydrogen, methyl, ethyl, isopropyl, tert-butyl or cyclopropyl;
R³ is Cl, F, CF₃, cyano, methyl, methoxy or cyclopropyl;
R⁴ is hydrogen, methyl or F;
X is N or CH;
Y is N or CH;
with the proviso that X and Y are not simultaneously CH;
or a pharmaceutically acceptable salt or acid addition salt, a racemic mixture, or its corresponding enantiomer, or mixture of enantiomers, and/or optical isomer and/or stereoisomer thereof, for example the following compounds:

3-(4-Chlorophenyl)-N-(2-cyclopropylpropan-2-yl)-5-(4-propan-2-ylpyrimidin-5-yl)-benzamide 3-(4-Chlorophenyl)-N-(2-cyclopropylpropan-2-yl)-5-(2-methylpyridin-3-yl)-benzamide N-(2-Cyclopropylpropan-2-yl)-3-(4-fluorophenyl)-5-(4-propan-2-ylpyrimidin-5-yl)-benzamide or N-(2-Cyclopropylpropan-2-yl)-3-(4-fluorophenyl)-5-(4-methylpyridin-3-yl)-benzamide.

One further object of the invention are compounds of formula IF,

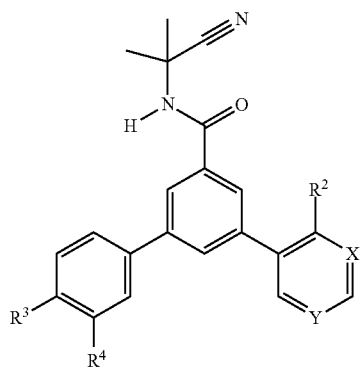

IF wherein
R² is hydrogen, methyl, ethyl, isopropyl, tert-butyl or cyclopropyl;
R³ is Cl, F, CF₃, cyano, methyl, methoxy or cyclopropyl;
R⁴ is hydrogen, methyl or F;
X is N or CH;
Y is N or CH;
with the proviso that X and Y are not simultaneously CH;
or a pharmaceutically acceptable salt or acid addition salt, a racemic mixture, or its corresponding enantiomer, or mixture of enantiomers, and/or optical isomer and/or stereoisomer thereof, for example the following compounds:

N-(2-Cyanopropan-2-yl)-3-(3-fluoro-4-methylphenyl)-5-(4-propan-2-yl-pyrimidin-5-yl)-benzamide N-(2-Cyanopropan-2-yl)-3-(4-fluoro-3-methylphenyl)-5-(4-propan-2-yl-pyrimidin-5-yl)-benzamide N-(2-Cyanopropan-2-yl)-3-(4-fluorophenyl)-5-(4-propan-2-yl-pyrimidin-5-yl)-benzamide N-(2-Cyanopropan-2-yl)-3-(4-propan-2-yl-pyrimidin-5-yl)-5-[4-(trifluoromethyl)-phenyl]-benzamide or 3-(4-Chlorophenyl)-N-(2-cyanopropan-2-yl)-5-(4-propan-2-yl-pyrimidin-5-yl)-benzamide.

One further object of the invention are compounds of formula IG,

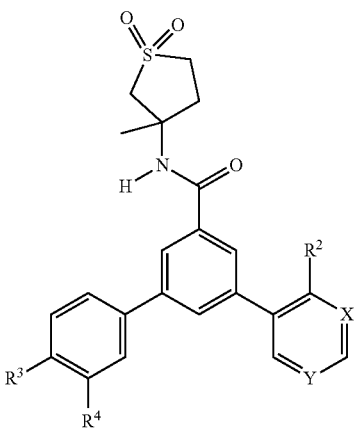

IG wherein
R² is hydrogen, methyl, ethyl, isopropyl, tert-butyl or cyclopropyl;
R³ is Cl, F, CF₃, cyano, methyl, methoxy or cyclopropyl;
R⁴ is hydrogen, methyl or F;
X is N or CH;
Y is N or CH;
with the proviso that X and Y are not simultaneously CH;
or a pharmaceutically acceptable salt or acid addition salt, a racemic mixture, or its corresponding enantiomer, or mixture of enantiomers, and/or optical isomer and/or stereoisomer thereof, for example the following compounds:

(RS)-3-(4-Chlorophenyl)-N-(3-methyl-1,1-dioxothiolan-3-yl)-5-(4-propan-2-ylpyrimidin-5-yl)-benzamide or (RS)-3-(4-Chlorophenyl)-N-(3-methyl-1,1-dioxothiolan-3-yl)-5-(2-methyl-pyridin-3-yl)-benzamide.

The preparation of compounds of formulas IA, IB, IC, ID, IE, IF and IG of the present invention may be carried out in sequential or convergent synthetic routes. Syntheses of the compounds of the invention are shown in the following schemes 1 to 6. The skills required for carrying out the reaction and purification of the resulting products are known to those skilled in the art. The substituents and indices used in the following description of the processes have the significance given herein before.

The compounds of formulas IA, IB, IC, ID, IE, IF and IG can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of IA, IB, IC, ID, IE, IF and IG and their pharmaceutically acceptable salts may be prepared by methods, known in the art, for example by the process variant described below, which process comprises a) reacting a compound of formula II

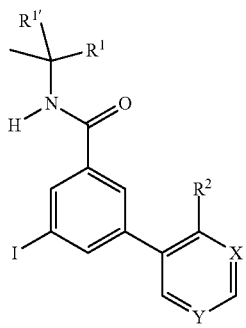

with a compound of formula III

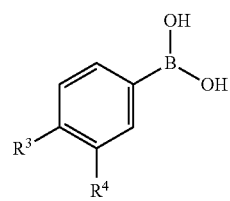

to a compound of formula I

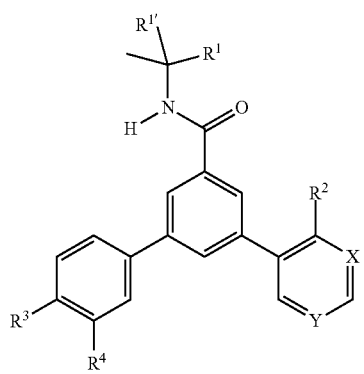

wherein the substituents are as described above, or if desired, converting the compounds obtained into pharmaceutically acceptable acid addition salts, or b) reacting a compound of formula IV

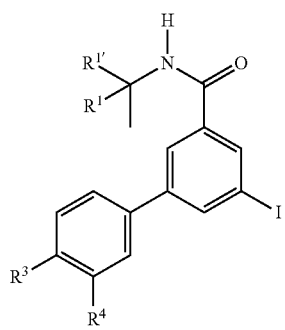

with a compound of formula V

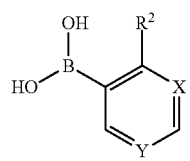

to a compound of formula I

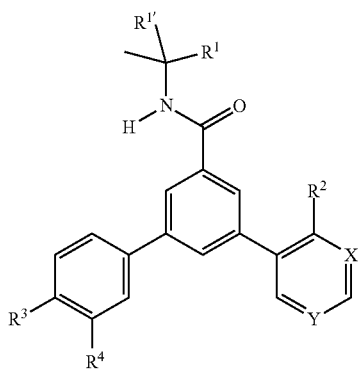

wherein the substituents are described above, or if desired, converting the compounds obtained into pharmaceutically acceptable acid addition salts, or c) reacting a compound of formula XVII

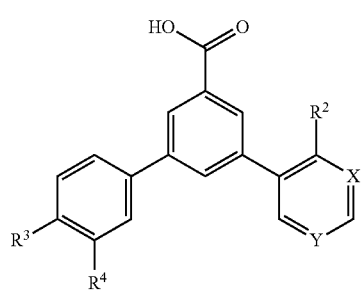

with a compound of formula VII

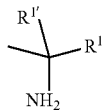

to a compound of formula I

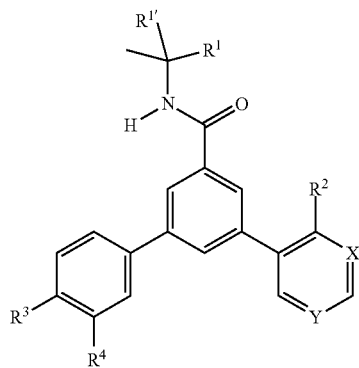

wherein the substituents are described above, or if desired, converting the compounds obtained into pharmaceutically acceptable acid addition salts, or d) reacting a compounds of formula XVIII

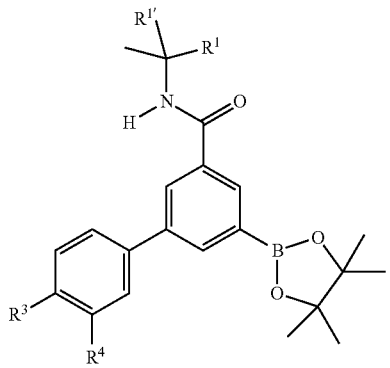

with a compound of formula XVI

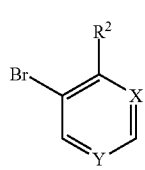

to a compound of formula I

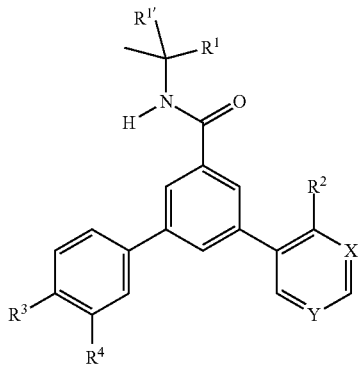

wherein the substituents are described above, or if desired, converting the compounds obtained into pharmaceutically acceptable acid addition salts.

The preparation of compounds of formulas IA, IB, IC, ID, IE, IF and IG is further described in more detail in scheme 1 to 6 and in examples 1-45.

In general the pyridine and pyrimidine derivatives I can either be prepared from the intermediate iodo derivatives II by coupling reaction with commercially available pyridine and pyrimidine boronic acids III

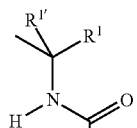 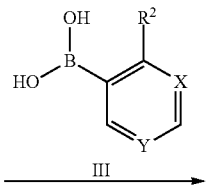

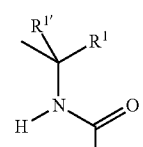

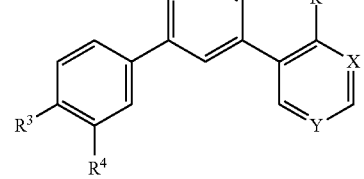

or by coupling reaction of the iodo derivatives IV with commercially available boronic acid derivatives V.

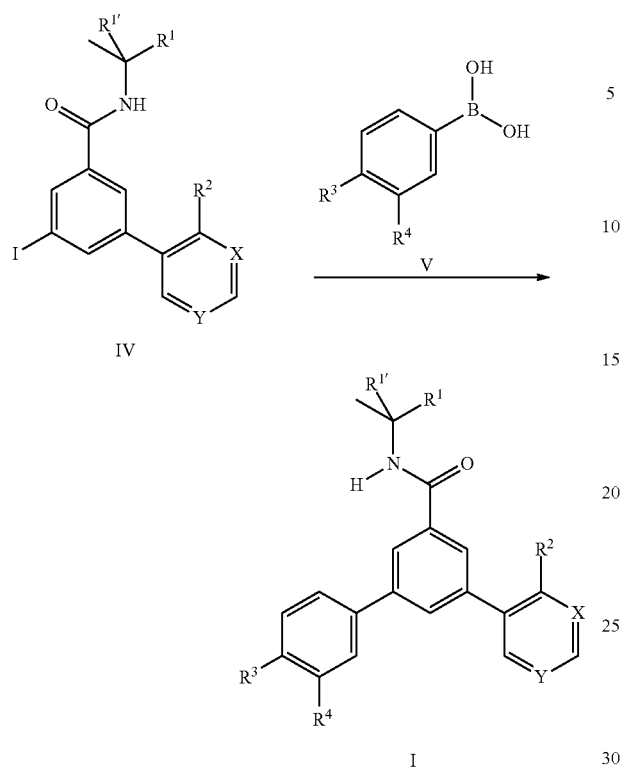

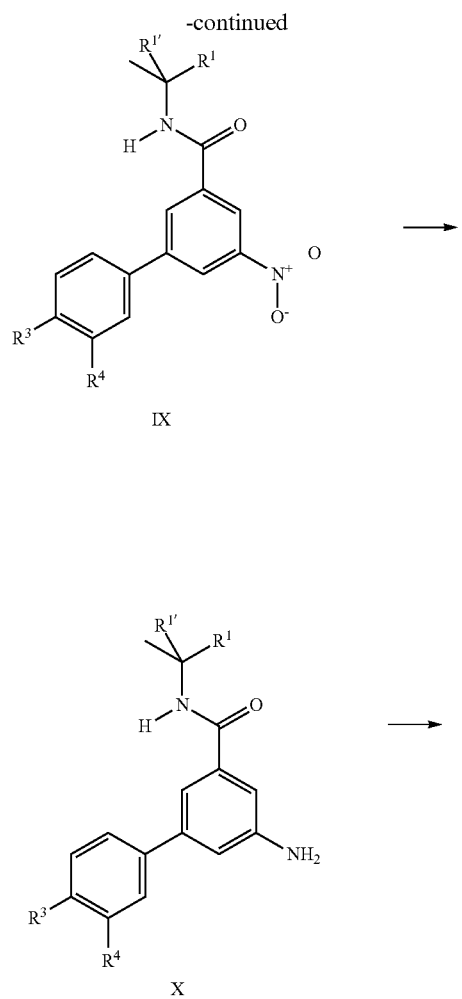

The iodo derivatives II can be prepared starting from commercially available 3-iodo-5-nitrobenzoic acid VI. Amide formation with the commercially available amines VII using standard conditions leads to the amides VIII which can coupled with commercially available boronic acid derivatives V to yield the nitro compounds IX which can be reduced with tin(II)chloride to yield the aniline derivatives X. Well known transformation of the aniline into iodine leads to the iodo building blocks II.

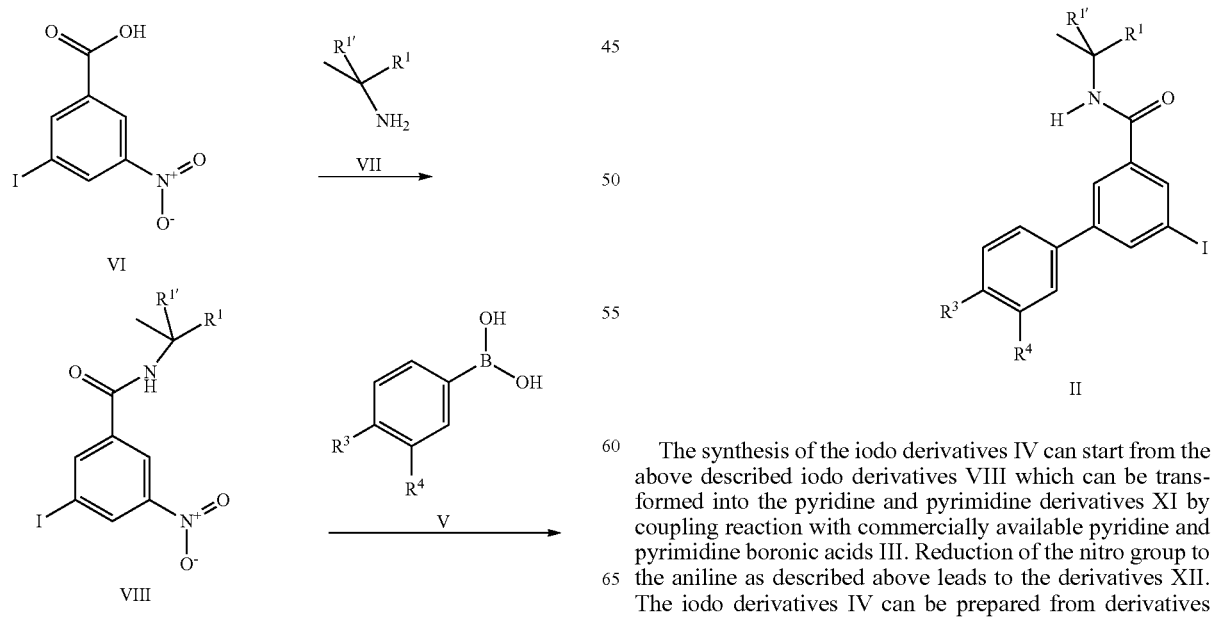

The synthesis of the iodo derivatives IV can start from the above described iodo derivatives VIII which can be transformed into the pyridine and pyrimidine derivatives XI by coupling reaction with commercially available pyridine and pyrimidine boronic acids III. Reduction of the nitro group to the aniline as described above leads to the derivatives XII. The iodo derivatives IV can be prepared from derivatives XII by known transformation of the aniline into the iodine.

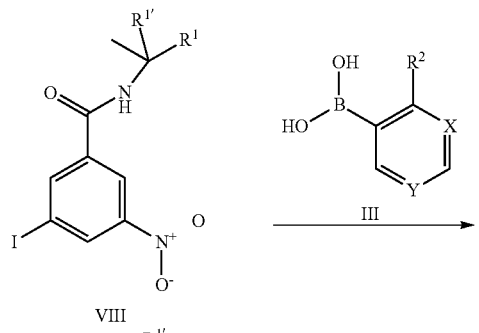

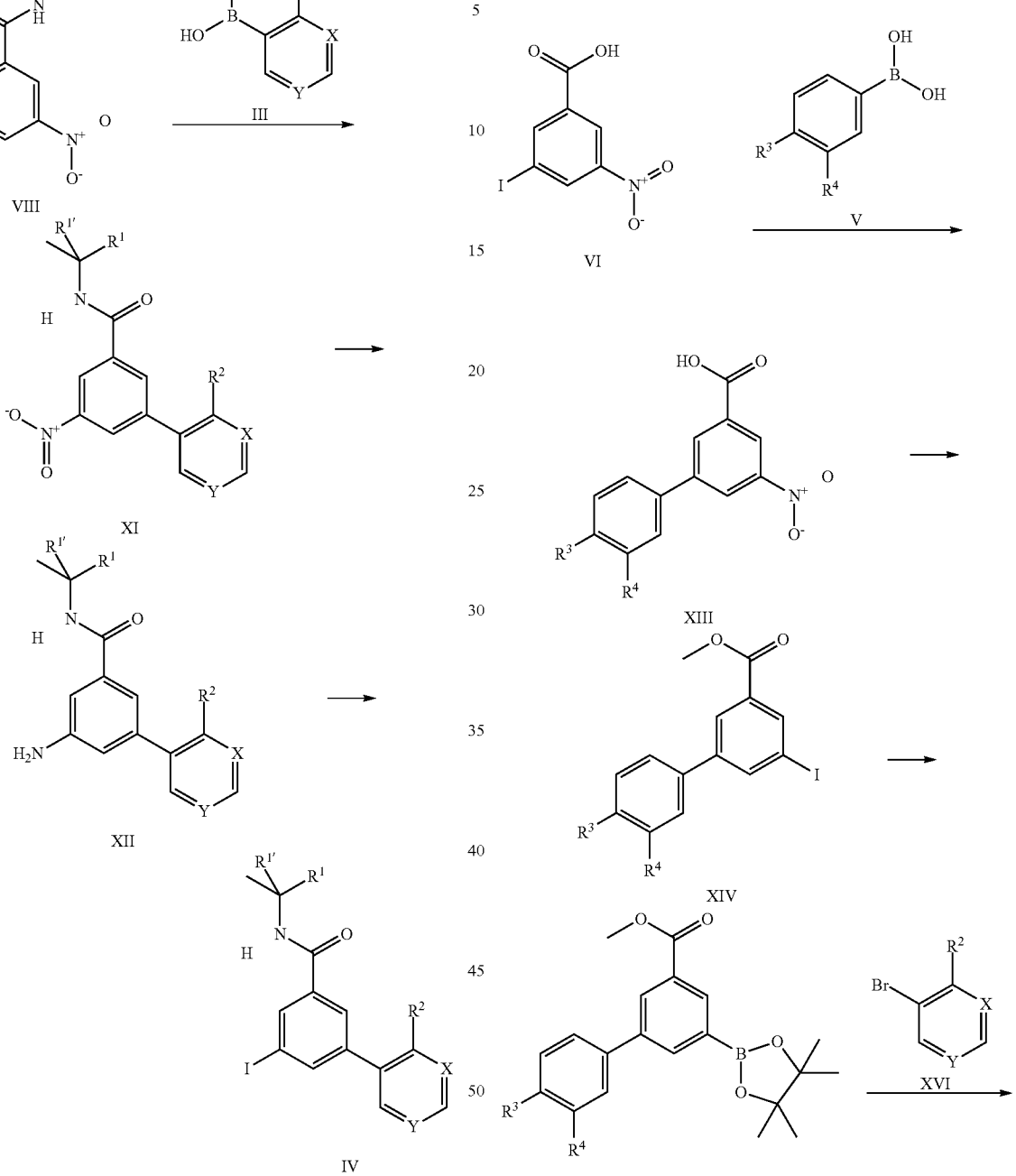

by known methods yielded the acid derivatives XVII. Amide formation with the commercially available amines VII using standard conditions leads to the final amides I.

An alternative route for the synthesis of the pyridine and pyrimidine derivatives I can start from the commercially available 3-iodo-5-nitrobenzoic acid VI. Coupling reaction with commercially available boronic acid derivatives V yields the nitro derivatives XII which can be transformed into the iodo derivatives XIV as described above by reduction of the nitro group followed by well-known transformation of the aniline into iodine, and subsequent ester formation. The iodo derivatives XIV can be transformed into the boronate derivatives XV by known methods. Coupling reaction with commercially available bromo pyridine and pyrimidine derivatives XVI, and subsequent ester hydrolysis

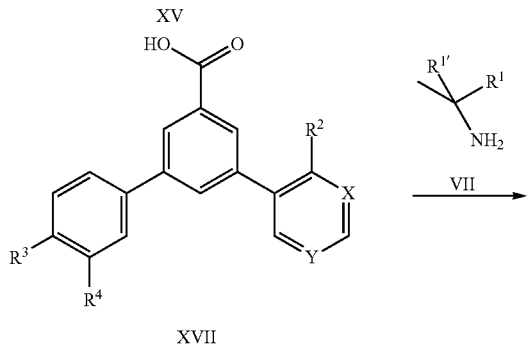

-continued

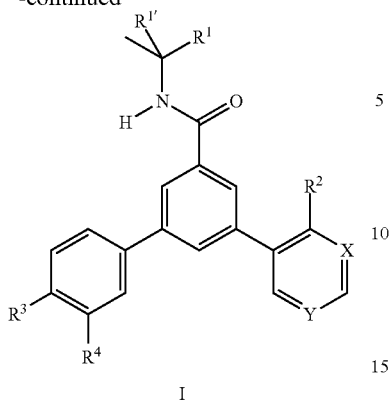

I

It is also possible to prepare the final compounds I by coupling reaction of the commercially available bromo pyridine and pyrimidine derivatives XVI with the boronates XVIII which can be prepared from the iodo building block II by known methods.

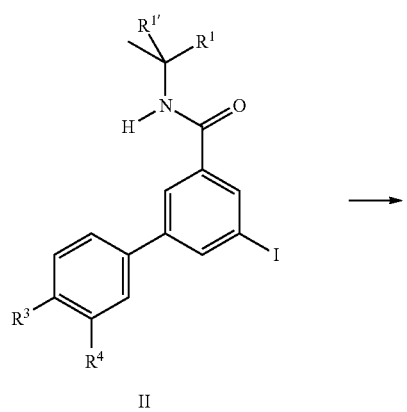

II

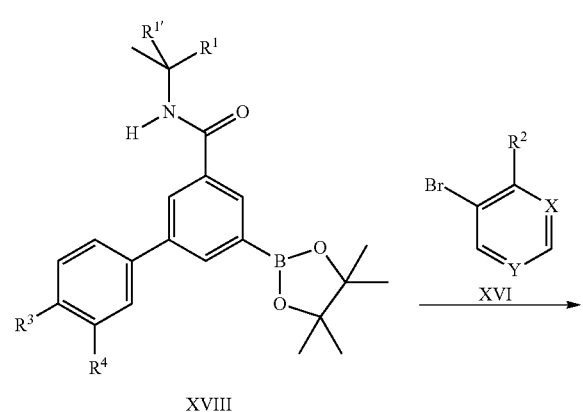

XVIII

-continued

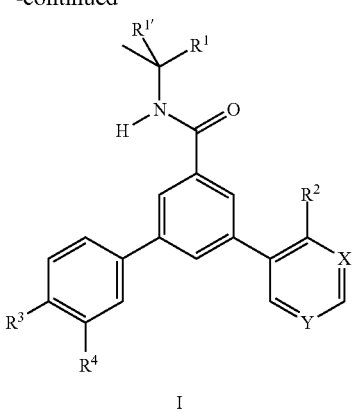

I

Generally speaking, the sequence of steps used to synthesize the compounds of formula I can also be modified in certain cases.

The compounds of formula I and their pharmaceutically usable addition salts possess valuable pharmaceutical properties. Specifically, it has been found that the compounds of the present invention are EAAT3 inhibitors for use in the treatment of schizophrenia, bipolar disorder, obsessive-compulsive disorder or autism spectrum disorders.

The compounds were investigated in accordance with the test given hereinafter.

Biological Assay and Data

The FLIPR Membrane Potential (FMP) Assay

HEK-293 cells stably expressing human EAAT3 were seeded at 55 000 cells/well in growth medium (DMEM glutamate free (Invitrogen 11960-044), 1% Pen Strep (10 ml/l GIBCO BRL N° 15140-023), 10% FCS non dialysed heat inactivated, 5 mg/l puromycin) in poly-D-lysine treated 96-well black microtiter plates with clear-bottom. After 24 h, the growth medium was removed and 100 μA/well of Krebs buffer (140 mM NaCl, 4.7 mM KCl, 2.5 mM $CaCl_2$, 1.2 mM $MgCl_2$, 11 mM HEPES, 10 mM D-glucose, pH=7.4) added. The cells were then loaded by adding 100 μl/well FMP assay dye (FLIPR Membrane Potential assay reagent, Molecular Devices). The 96-well plates were then incubated at 37° C. for 1 h. The depolarization of the cells will cause more dye to enter in the cells, where it will bind to intracellular proteins and lipids and cause an increase in the fluorescence signal. Antagonist potency at human EAAT3 was determined by using L-glutamate as agonist at a concentration which gives 80% of the maximum response. The antagonists were applied 15 min before the application of the agonist L-glutamate. The assays were performed at room temperature and measurements done by using a Fluorometric Imaging Plate Reader (FLIPR, Molecular Devices) and filter #2. Responses were measured as peak increase in fluorescence minus basal (i.e. fluorescence without addition of L-glutamate). Kb was determined using the Cheng-Prusoff equation $Kb=IC_{50}/[1+(A/EC_{50})]$, where $IC_{50}$ is the concentration of the antagonist producing 50% inhibition, A is the concentration of the agonist against which the $IC_{50}$ is being determined (at $EC_{80}$) and $EC_{50}$ is the concentration of the agonist producing 50% inhibition.

List of Examples and Data:
| | Structure | Compound name | EAAT3 Kb [uM] |
|---|---|---|---|
| 1 | 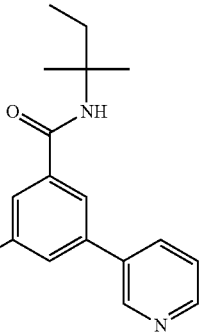 | N-(2-Methylbutan-2-yl)-3-(4-methylphenyl)-5-pyridin-3-ylbenzamide | 0.325 |
| 2 | 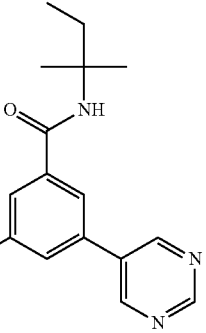 | N-(2-Methylbutan-2-yl)-3-(4-methylphenyl)-5-pyrimidin-5-ylbenzamide | 0.22 |
| 3 | 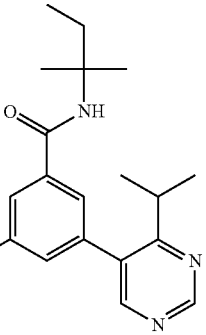 | N-(2-Methylbutan-2-yl)-3-(4-methylphenyl)-5-(4-propan-2-ylpyrimidin-5-yl)-benzamide | 0.23 |
| 4 | 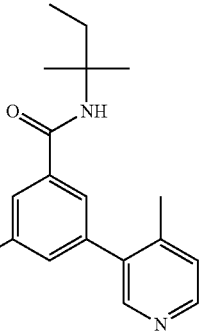 | N-(2-Methylbutan-2-yl)-3-(4-methylphenyl)-5-(4-methylpyridin-3-yl)-benzamide | 0.29 |

-continued

| | Structure | Compound name | EAAT3 Kb [uM] |
|---|---|---|---|
| 5 | 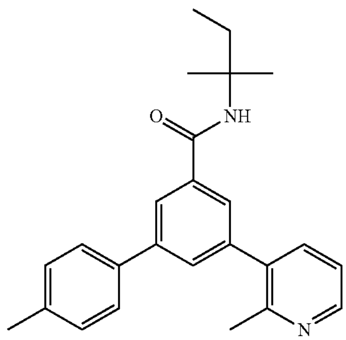 [SMILES: CCC(C)(C)NC(=O)c1cc(-c2ccc(C)cc2)cc(-c2cccnc2C)c1] | N-(2-Methylbutan-2-yl)-3-(4-methylphenyl)-5-(2-methylpyridin-3-yl)-benzamide | 0.25 |
| 6 | 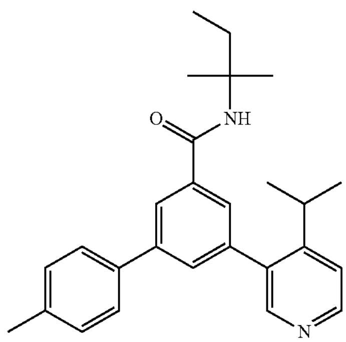 [SMILES: CCC(C)(C)NC(=O)c1cc(-c2ccc(C)cc2)cc(-c2cnccc2C(C)C)c1] | N-(2-Methylbutan-2-yl)-3-(4-methylphenyl)-5-(4-propan-2-ylpyridin-3-yl)-benzamide | 0.38 |
| 7 | 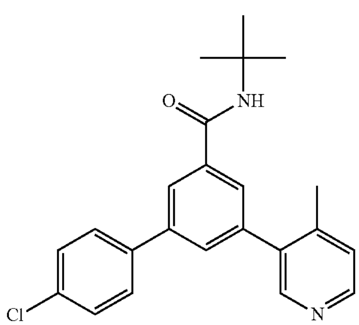 | N-tert-Butyl-3-(4-chlorophenyl)-5-(4-methylpyridin-3-yl)-benzamide | 0.31 |
| 8 | 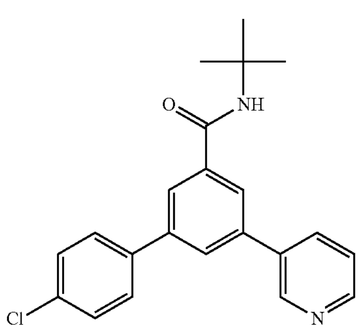 [SMILES: CC(C)(C)NC(=O)c1cc(-c2ccc(Cl)cc2)cc(-c2cccnc2)c1] | N-tert-Butyl-3-(4-chlorophenyl)-5-pyridin-3-ylbenzamide | 0.35 |

-continued

| | Structure | Compound name | EAAT3 Kb [uM] |
|---|---|---|---|
| 9 | 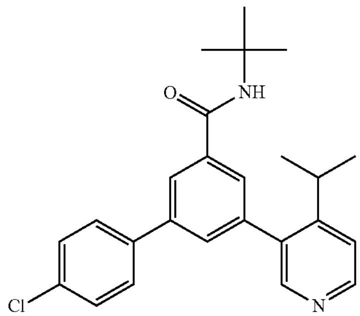 [SMILES: CC(C)c1ccncc1-c1cc(C(=O)NC(C)(C)C)cc(-c2ccc(Cl)cc2)c1] | N-tert-Butyl-3-(4-chlorophenyl)-5-(4-propan-2-ylpyridin-3-yl)-benzamide | 0.54 |
| 10 | 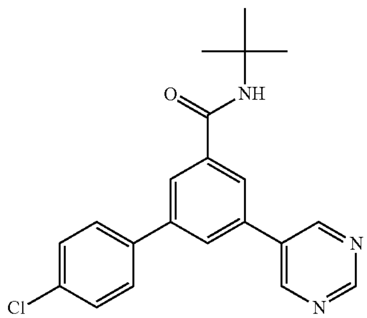 [SMILES: CC(C)(C)NC(=O)c1cc(-c2ccc(Cl)cc2)cc(-c2cncnc2)c1] | N-tert-Butyl-3-(4-chlorophenyl)-5-pyrimidin-5-ylbenzamide | 0.27 |
| 11 | 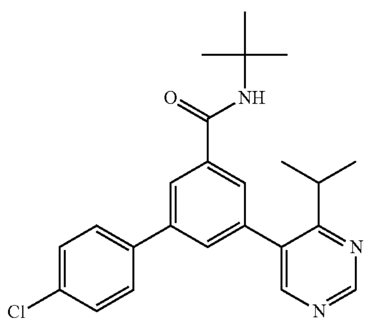 [SMILES: CC(C)c1ncncc1-c1cc(C(=O)NC(C)(C)C)cc(-c2ccc(Cl)cc2)c1] | N-tert-Butyl-3-(4-chlorophenyl)-5-(4-propan-2-ylpyrimidin-5-yl)-benzamide | 0.23 |
| 12 | 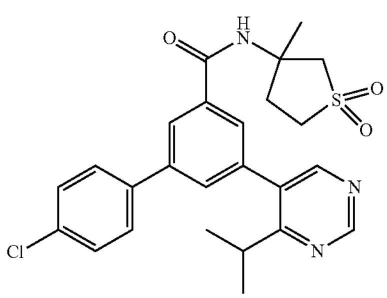 [SMILES: CC(C)c1ncncc1-c1cc(C(=O)NC2(C)CCS(=O)(=O)C2)cc(-c2ccc(Cl)cc2)c1] | (RS)-3-(4-Chlorophenyl)-N-(3-methyl-1,1-dioxothiolan-3-yl)-5-(4-propan-2-ylpyrimidin-5-yl)-benzamide | 0.31 |
| 13 | 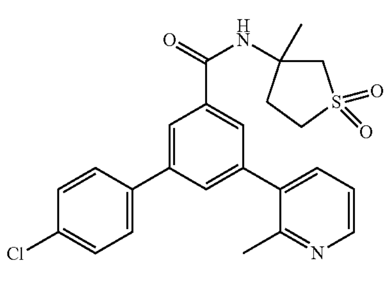 [SMILES: Cc1ncccc1-c1cc(C(=O)NC2(C)CCS(=O)(=O)C2)cc(-c2ccc(Cl)cc2)c1] | (RS)-3-(4-Chlorophenyl)-N-(3-methyl-1,1-dioxothiolan-3-yl)-5-(2-methyl-pyridin-3-yl)-benzamide | 0.51 |

-continued

| | Structure | Compound name | EAAT3 Kb [uM] |
|---|---|---|---|
| 14 | 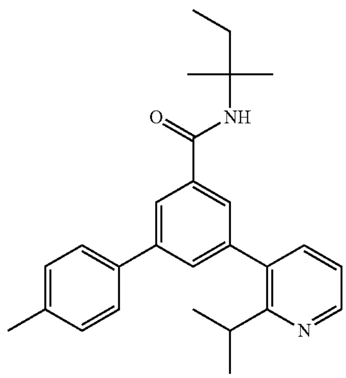 [SMILES: CCC(C)(C)NC(=O)c1cc(-c2ccc(C)cc2)cc(-c2cccnc2C(C)C)c1] | N-(2-Methylbutan-2-yl)-3-(4-methylphenyl)-5-(2-propan-2-ylpyridin-3-yl)-benzamide | 0.57 |
| 15 | 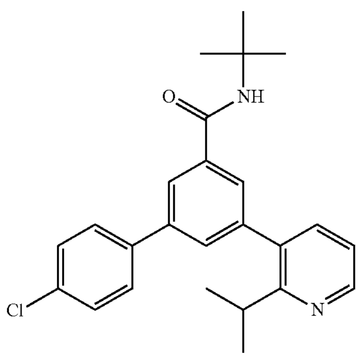 [SMILES: CC(C)c1ncccc1-c1cc(C(=O)NC(C)(C)C)cc(-c2ccc(Cl)cc2)c1] | N-tert-Butyl-3-(4-chlorophenyl)-5-(2-propan-2-ylpyridin-3-yl)-benzamide | 0.63 |
| 16 | 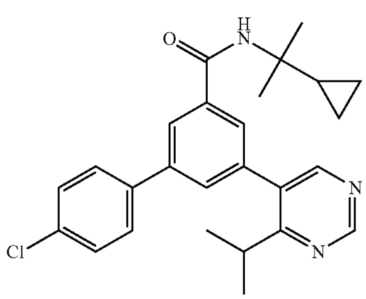 [SMILES: CC(C)c1ncncc1-c1cc(C(=O)NC(C)(C)C2CC2)cc(-c2ccc(Cl)cc2)c1] | 3-(4-Chlorophenyl)-N-(2-cyclopropylpropan-2-yl)-5-(4-propan-2-ylpyrimidin-5-yl)-benzamide | 0.42 |
| 17 | 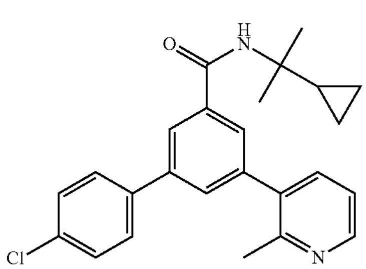 [SMILES: Cc1ncccc1-c1cc(C(=O)NC(C)(C)C2CC2)cc(-c2ccc(Cl)cc2)c1] | 3-(4-Chlorophenyl)-N-(2-cyclopropylpropan-2-yl)-5-(2-methylpyridin-3-yl)-benzamide | 0.64 |

-continued

| | Structure | Compound name | EAAT3 Kb [uM] |
|---|---|---|---|
| 18 | 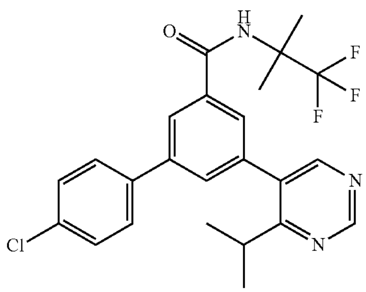 [SMILES: CC(C)c1ncncc1-c1cc(C(=O)NC(C)(C)C(F)(F)F)cc(-c2ccc(Cl)cc2)c1] | 3-(4-Chlorophenyl)-5-(4-propan-2-ylpyrimidin-5-yl)-N-(1,1,1-trifluoro-2-methylpropan-2-yl)-benzamide | 0.25 |
| 19 | 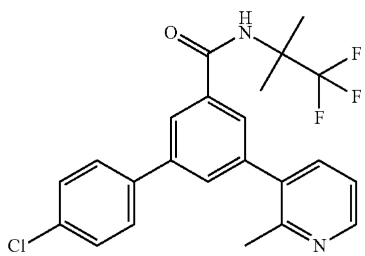 [SMILES: Cc1ncccc1-c1cc(C(=O)NC(C)(C)C(F)(F)F)cc(-c2ccc(Cl)cc2)c1] | 3-(4-Chlorophenyl)-5-(2-methylpyridin-3-yl)-N-(1,1,1-trifluoro-2-methylpropan-2-yl)-benzamide | 0.34 |
| 20 | 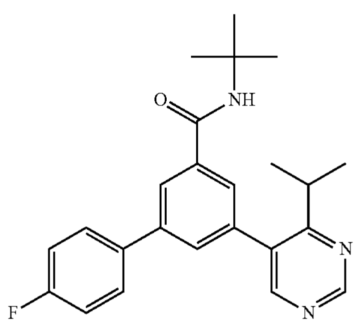 [SMILES: CC(C)c1ncncc1-c1cc(C(=O)NC(C)(C)C)cc(-c2ccc(F)cc2)c1] | N-tert-Butyl-3-(4-fluorophenyl)-5-(4-propan-2-ylpyrimidin-5-yl)-benzamide | 0.081 |
| 21 | 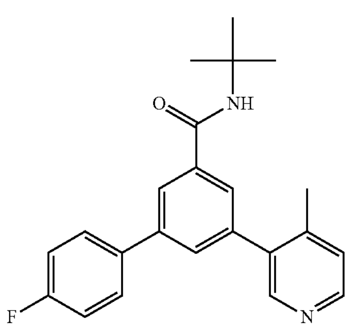 [SMILES: Cc1ccncc1-c1cc(C(=O)NC(C)(C)C)cc(-c2ccc(F)cc2)c1] | N-tert-Butyl-3-(4-fluorophenyl)-5-(4-methylpyridin-3-yl)-benzamide | 0.2 |
| 22 | 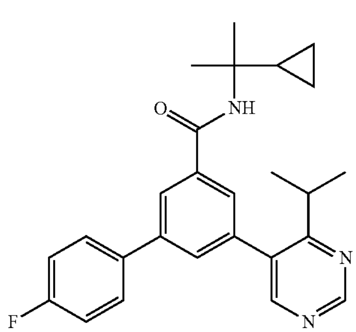 [SMILES: CC(C)c1ncncc1-c1cc(C(=O)NC(C)(C)C2CC2)cc(-c2ccc(F)cc2)c1] | N-(2-Cyclopropylpropan-2-yl)-3-(4-fluorophenyl)-5-(4-propan-2-ylpyrimidin-5-yl)-benzamide | 0.057 |

-continued
| | Structure | Compound name | EAAT3 Kb [uM] |
|---|---|---|---|
| 23 | 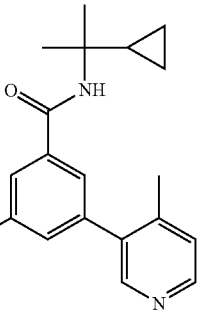 | N-(2-Cyclopropylpropan-2-yl)-3-(4-fluorophenyl)-5-(4-methylpyridin-3-yl)-benzamide | 0.078 |
| 24 | 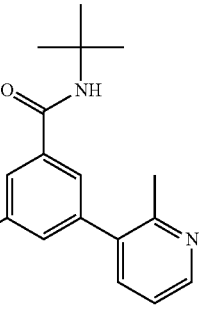 | N-tert-Butyl-3-(4-fluorophenyl)-5-(2-methylpyridin-3-yl)-benzamide | 0.17 |
| 25 | 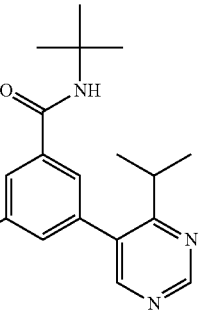 | N-tert-Butyl-3-(4-methylphenyl)-5-(4-propan-2-ylpyrimidin-5-yl)-benzamide | 0.25 |
| 26 | 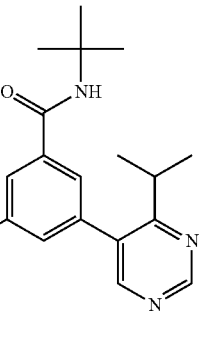 | N-tert-Butyl-3-(3,4-difluorophenyl)-5-(4-propan-2-ylpyrimidin-5-yl)-benzamide | 0.1 |

-continued

| | Structure | Compound name | EAAT3 Kb [uM] |
|---|---|---|---|
| 27 | 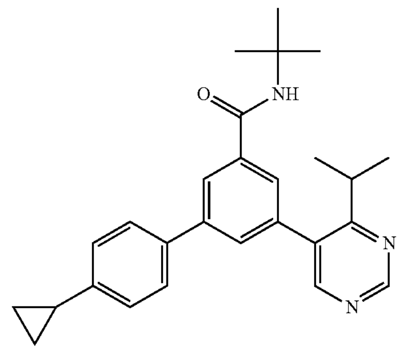 [SMILES: CC(C)c1ncncc1-c1cc(C(=O)NC(C)(C)C)cc(-c2ccc(C3CC3)cc2)c1] | N-tert-Butyl-3-(4-cyclopropylphenyl)-5-(4-propan-2-ylpyrimidin-5-yl)-benzamide | 0.18 |
| 28 | 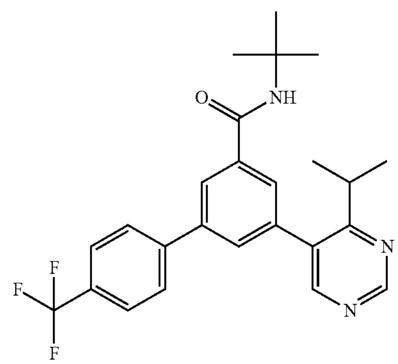 [SMILES: CC(C)c1ncncc1-c1cc(C(=O)NC(C)(C)C)cc(-c2ccc(C(F)(F)F)cc2)c1] | N-tert-Butyl-3-(4-propan-2-ylpyrimidin-5-yl)-5-[4-(trifluoromelhyl)-phenyl]-benzamide | 0.31 |
| 29 | 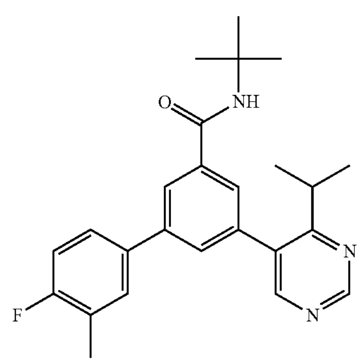 [SMILES: Cc1cc(-c2cc(C(=O)NC(C)(C)C)cc(-c3cncnc3C(C)C)c2)ccc1F] | N-tert-Butyl-3-(4-fluoro-3-methylphenyl)-5-(4-propan-2-ylpyrimidin-5-yl)-benzamide | 0.72 |
| 30 | 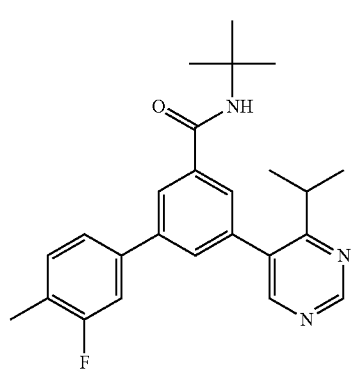 [SMILES: Cc1ccc(-c2cc(C(=O)NC(C)(C)C)cc(-c3cncnc3C(C)C)c2)cc1F] | N-tert-Butyl-3-(3-fluoro-4-methylphenyl)-5-(4-propan-2-ylpyrimidin-5-yl)-benzamide | 0.77 |

-continued

| | Structure | Compound name | EAAT3 Kb [uM] |
|---|---|---|---|
| 31 | 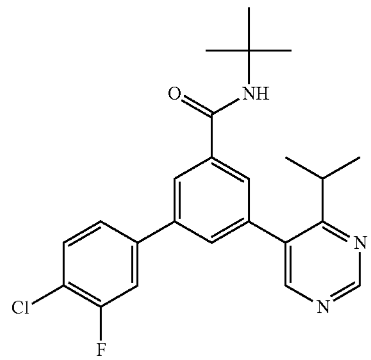 [SMILES: CC(C)c1ncncc1-c1cc(C(=O)NC(C)(C)C)cc(-c2ccc(Cl)c(F)c2)c1] | N-tert-Butyl-3-(4-chloro-3-fluorophenyl)-5-(4-propan-2-ylpyrimidin-5-yl)-benzamide | 0.32 |
| 32 | 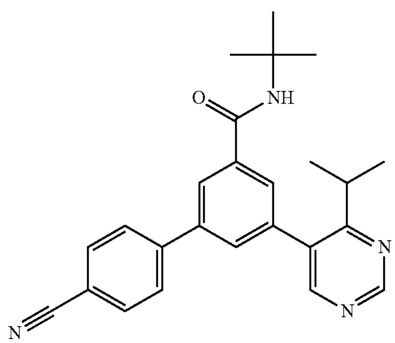 [SMILES: CC(C)c1ncncc1-c1cc(C(=O)NC(C)(C)C)cc(-c2ccc(C#N)cc2)c1] | N-tert-Butyl-3-(4-cyanophenyl)-5-(4-propan-2-ylpyrimidin-5-yl)-benzamide | 0.57 |
| 33 | 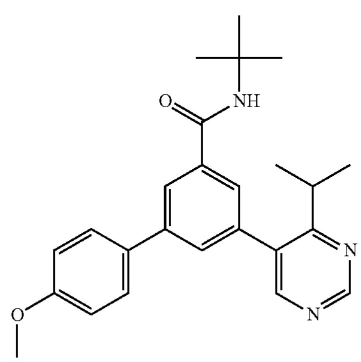 [SMILES: COc1ccc(-c2cc(C(=O)NC(C)(C)C)cc(-c3cncnc3C(C)C)c2)cc1] | N-tert-Butyl-3-(4-methoxyphenyl)-5-(4-propan-2-ylpyrimidin-5-yl)-benzamide | 0.54 |
| 34 | 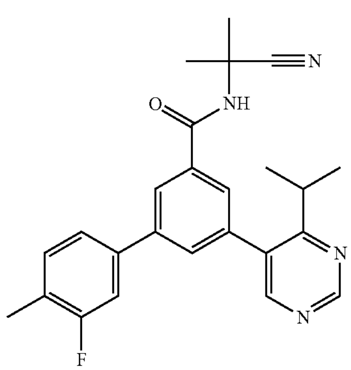 [SMILES: Cc1ccc(-c2cc(C(=O)NC(C)(C)C#N)cc(-c3cncnc3C(C)C)c2)cc1F] | N-(2-Cyanopropan-2-yl)-3-(3-fluoro-4-methylphenyl)-5-(4-propan-2-yl-pyrimidin-5-yl)-benzamide | 0.4 |

-continued
| | Structure | Compound name | EAAT3 Kb [uM] |
|---|---|---|---|
| 35 | 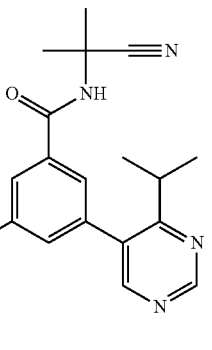 | N-(2-Cyanopropan-2-yl)-3-(4-fluoro-3-methylphenyl)-5-(4-propan-2-yl-pyrimidin-5-yl)-benzamide | 0.35 |
| 36 | 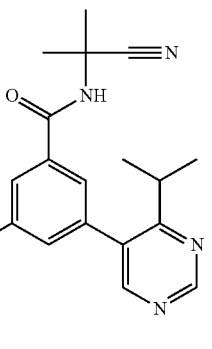 | N-(2-Cyanopropan-2-yl)-3-(4-fluorophenyl)-5-(4-propan-2-yl-pyrimidin-5-yl)-benzamide | 0.27 |
| 37 | 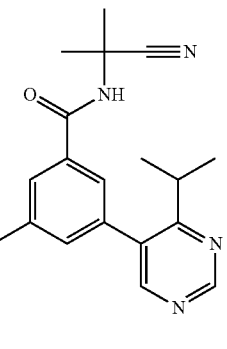 | N-(2-Cyanopropan-2-yl)-3-(4-propan-2-yl-pyrimidin-5-yl)-5-[4-(trifluoromethyl)-phenyl]-benzamide | 0.21 |
| 38 | 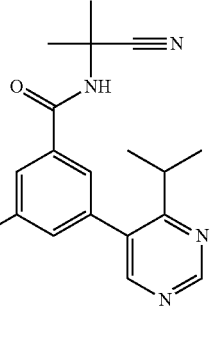 | 3-(4-Chlorophenyl)-N-(2-cyanopropan-2-yl)-5-(4-propan-2-yl-pyrimidin-5-yl)-benzamide | 0.16 |

-continued

| | Structure | Compound name | EAAT3 Kb [uM] |
|---|---|---|---|
| 39 | 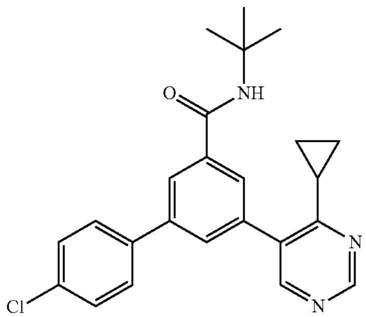 [SMILES: CC(C)(C)NC(=O)c1cc(-c2ccc(Cl)cc2)cc(-c2cncnc2C2CC2)c1] | N-tert-Butyl-3-(4-chlorophenyl)-5-(4-cyclopropyl-pyrimidin-5-yl)-benzamide | 0.27 |
| 40 | 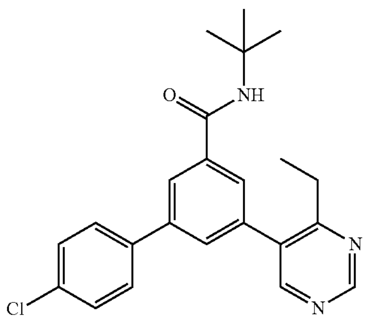 [SMILES: CCc1ncncc1-c1cc(C(=O)NC(C)(C)C)cc(-c2ccc(Cl)cc2)c1] | N-tert-Butyl-3-(4-chlorophenyl)-5-(4-ethyl-pyrimidin-5-yl)-benzamide | 0.14 |
| 41 | 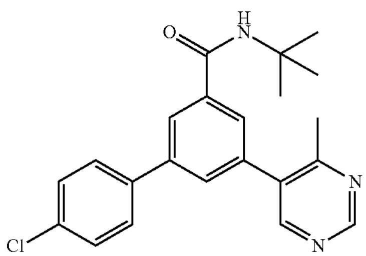 [SMILES: Cc1ncncc1-c1cc(C(=O)NC(C)(C)C)cc(-c2ccc(Cl)cc2)c1] | N-tert-Butyl-3-(4-chlorophenyl)-5-(4-methyl-pyrimidin-5-yl)-benzamide | |
| 42 | 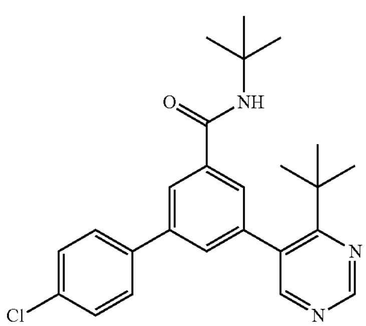 [SMILES: CC(C)(C)NC(=O)c1cc(-c2ccc(Cl)cc2)cc(-c2cncnc2C(C)(C)C)c1] | N-tert-Butyl-3-(4-tert-butyl-pyrimidin-5-yl)-5-(4-chlorophenyl)-benzamide | |
| 43 | 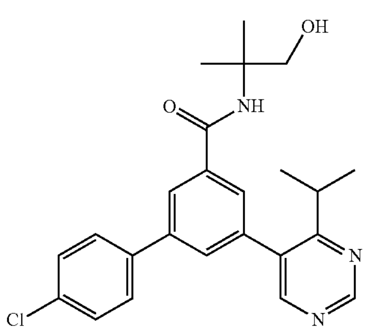 [SMILES: CC(C)c1ncncc1-c1cc(C(=O)NC(C)(C)CO)cc(-c2ccc(Cl)cc2)c1] | 3-(4-Chlorophenyl)-N-(1-hydroxy-2-methylpropan-2-yl)-5-(4-propan-2-yl-pyrimidin-5-yl)-benzamide | |

-continued

| | Structure | Compound name | EAAT3 Kb [uM] |
|---|---|---|---|
| 44 | 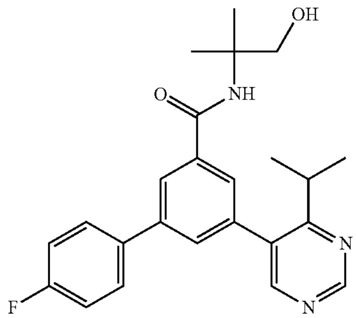 [SMILES: CC(C)c1ncncc1-c1cc(C(=O)NC(C)(C)CO)cc(-c2ccc(F)cc2)c1] | 3-(4-Fluorophenyl)-N-(1-hydroxy-2-methylpropan-2-yl)-5-(4-propan-2-yl-pyrimidin-5-yl)-benzamide | |
| 45 | 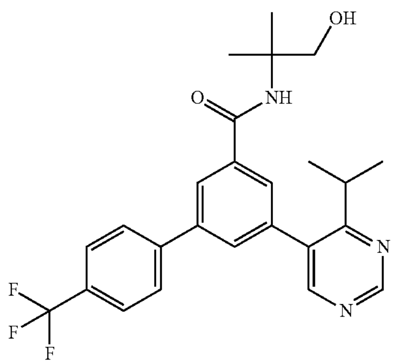 [SMILES: CC(C)c1ncncc1-c1cc(C(=O)NC(C)(C)CO)cc(-c2ccc(C(F)(F)F)cc2)c1] | N-(1-Hydroxy-2-methylpropan-2-yl)-3-(4-propan-2-yl-pyrimidin-5-yl)-5-[4-(trifluoromethyl)-phenyl]-benzamide | |

The compounds of formula (I) and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula (I) and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like; depending on the nature of the active substance no carriers are, however, usually required in the case of soft gelatin capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula (I) or pharmaceutically acceptable salts thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers.

As further mentioned earlier, the use of the compounds of formula (I) for the preparation of medicaments useful in the prevention and/or the treatment of the above recited diseases is also an object of the present invention.

The dosage can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

Preparation of Pharmaceutical Compositions Comprising Compounds of the Invention Tablets of the following composition are manufactured in the usual manner:

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Capsules of the following composition are manufactured:

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

A compound of formula I lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Injection solutions of the following composition are manufactured:

| ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

Manufacturing Procedure

A compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

EXPERIMENTAL SECTION

Intermediates

Intermediate 1: N-tert-Butyl-3-(4-chlorophenyl)-5-iodobenzamide

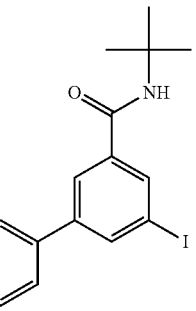

Step A

To a stirred solution of commercially available 3-iodo-5-nitrobenzoic acid (2 g, 6.83 mmol) in THF (49.1 ml) was added at room temperature N,N-diisopropylethylamine (2.21 g, 2.98 ml, 17.1 mmol), 2-methylpropan-2-amine (611 mg, 878 µl, 8.19 mmol) and O-(benzotriazol-1-yl)-N,N,N',N'-tetramethyluronium tetrafluoroborate (TBTU) (3.51 g, 10.9 mmol) The reaction mixture was stirred at room temperature for 4 h, evaporated and the residue purified by flash chromatography on silica gel [heptane/ethyl acetate (0-50%)] to yield N-tert-butyl-3-iodo-5-nitrobenzamide (2.31 g, 97%) as an off-white solid, MS (ISP) m/z=349.0 [(M+H)$^+$], mp 166° C.

Step B

A mixture of N-tert-butyl-3-iodo-5-nitrobenzamide (2.3 g, 6.61 mmol) and (4-chlorophenyl)boronic acid (1.34 g, 8.59 mmol) in 1,2-dimethoxyethane (44 ml) and 2M Na$_2$CO$_3$ (11 ml, 22 mmol) was purged with argon in an ultrasonic bath for 5 min, triphenylphosphine (347 mg, 1.32 mmol) and palladium(II)acetate (148 mg, 661 µmol) were added and the reaction mixture was stirred for 3 h under reflux conditions. The reaction mixture poured into water (50 ml) and extracted with ethylacetate (2×50 ml). The combined organic layers were washed with brine (40 ml), dried (MgSO$_4$) and evaporated to give the crude product (3.09 g) as brown solid, which was purified by flash chromatography on silica gel [heptane/ethyl acetate (0-50%)] to yield N-tert-butyl-3-(4-chlorophenyl)-5-nitrobenzamide (2.38 g, 92%) as a brown solid, MS (ISP) m/z=333.1 [(M+H)$^+$], mp 186° C.

Step C

To a stirred solution of N-tert-butyl-3-(4-chlorophenyl)-5-nitrobenzamide (2.38 g, 6.58 mmol) in MeOH (49.8 ml) was added at room temperature tin(II)chloride dihydrate (5.94 g, 26.3 mmol) and the reaction mixture was stirred under reflux conditions for 2 h, evaporated, water (50 ml) and 2N NaOH (50 ml) were added and the mixture was extracted with ethyl acetate (2×75 ml). The combined organic layers were washed with water (50 ml) and brine (50 ml), dried (MgSO$_4$) and evaporated. The crude product (brown solid, 2.08 g) was purified by flash chromatography on silica gel [dichloromethane/MeOH (1-5%)] to yield 3-amino-N-tert-butyl-5-(4-chlorophenyl)-benzamide (1.90 g, 95%) as a light brown solid, MS (ISP) m/z=303.1 [(M+H)⁺], mp 231° C.

Step D

A mixture of 3-amino-N-tert-butyl-5-(4-chlorophenyl)-benzamide (1.899 g, 6.27 mmol), isoamyl nitrite (4.59 g, 5.27 ml, 37.6 mmol) and diiodomethane (10.2 g, 3.07 ml, 37.6 mmol) was stirred at room temperature for 1 h, and afterwards at 65° C. for 5 h. The reaction mixture was cooled to room temperature, toluene (30 ml) was added and the mixture was evaporated to dryness which was repeated 3 times. The residue was purified by flash chromatography on silica gel [heptane/ethy acetate (0-40%)] to yield the title compound (1.41 g, 55%) as light yellow foam, MS (ISP) m/z=414.0 [(M+H)⁺].

Intermediate 2: (RS)-3-(4-Chlorophenyl)-5-iodo-N-(3-methyl-1,1-dioxothiolan-3-yl)-benzamide

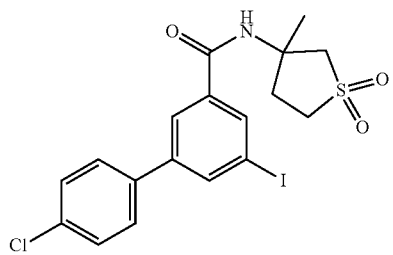 [SMILES: CC1(NC(=O)c2cc(I)cc(-c3ccc(Cl)cc3)c2)CCS(=O)(=O)C1]

Step A 3-(4-Chlorophenyl)-5-nitrobenzoic acid, light yellow solid (3.29 g, 99%), MS (ISN) m/z=276.1 [(M−H)⁻], mp 206° C., was prepared in accordance with the general method of intermediate 1, step B, from commercially available 3-iodo-5-nitrobenzoic acid (3.66 g, 11.9 mmol) and commercially available (4-chlorophenyl)-boronic acid (2.04 g, 13.1 mmol).

Step B (RS)-3-(4-Chlorophenyl)-N-(3-methyl-1,1-dioxothiolan-3-yl)-5-nitrobenzamide, light yellow foam (1.41 g, 91%), MS (ISP) m/z=409.1 [(M+H)⁺], was prepared in accordance with the general method of intermediate 1, step A, from 3-(4-chlorophenyl)-5-nitrobenzoic acid (1.05 g, 3.78 mmol) and commercially available (RS)-3-amino-3-methyltetrahydrothiophene 1,1-dioxide (677 mg, 4.54 mmol).

Step C (RS)-3-Amino-5-(4-chlorophenyl)-N-(3-methyl-1,1-dioxothiolan-3-yl)-benzamide, white solid (1.19 g, 91%), MS (ISP) m/z=379.1 [(M+H)⁺], mp 197° C., was prepared in accordance with the general method of intermediate 1, step C, from (RS)-3-(4-chlorophenyl)-N-(3-methyl-1,1-dioxothiolan-3-yl)-5-nitrobenzamide (1.41 g, 3.45 mmol).

Step D

The title compound, off-white foam (1.175 g, 77%), MS (ISP) m/z=490.1 [(M+H)⁺], was prepared in accordance with the general method of intermediate 1, step D, from (RS)-3-amino-5-(4-chlorophenyl)-N-(3-methyl-1,1-dioxothiolan-3-yl)-benzamide (1.18 g, 3.11 mmol).

Intermediate 3: 3-(4-Chlorophenyl)-N-(2-cyclopropylpropan-2-yl)-5-iodobenzamide

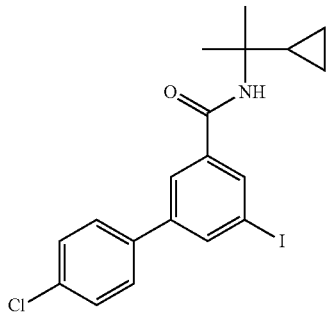 [SMILES: CC(C)(NC(=O)c1cc(I)cc(-c2ccc(Cl)cc2)c1)C1CC1]

Step A 3-(4-Chlorophenyl)-N-(2-cyclopropylpropan-2-yl)-5-nitrobenzamide, light yellow solid (1.25 g, 92%), MS (ISP) m/z=359.1 [(M+H)⁺], mp 172° C., was prepared in accordance with the general method of intermediate 1, step A, from 3-(4-chlorophenyl)-5-nitrobenzoic acid (intermediate 2, step A) (1.05 g, 3.78 mmol) and commercially available 2-cyclopropylpropan-2-amine (0.45 g, 4.54 mmol).

Step B

3-Amino-5-(4-chlorophenyl)-N-(2-cyclopropylpropan-2-yl)-benzamide, light yellow solid (0.98 g, 85%), MS (ISP) m/z=329.1 [(M+H)⁺], mp 199° C., was prepared in accordance with the general method of intermediate 1, step C, from 3-(4-chlorophenyl)-N-(2-cyclopropyl-propan-2-yl)-5-nitrobenzamide (1.25 g, 3.48 mmol).

Step C

The title compound, light brown solid (1.0 g, 77%), MS (ISP) m/z=440.1 [(M+H)⁺], mp 152° C., was prepared in accordance with the general method of intermediate 1, step D, from 3-amino-5-(4-chlorophenyl)-N-(2-cyclopropylpropan-2-yl)-benzamide (0.97 g, 2.95 mmol).

Intermediate 4: 3-(4-Chlorophenyl)-5-iodo-N-(1,1,1-trifluoro-2-methylpropan-2-yl)-benzamide

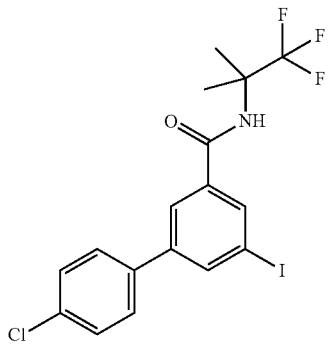 [SMILES: CC(C)(NC(=O)c1cc(I)cc(-c2ccc(Cl)cc2)c1)C(F)(F)F]

Step A 3-(4-Chlorophenyl)-5-nitro-N-(1,1,1-trifluoro-2-methylpropan-2-yl)-benzamide, off-white solid (0.63 g, 43%), MS (ISP) m/z=387.1 [(M+H)⁺], mp 180° C., was prepared in accordance with the general method of intermediate 1, step A, from 3-(4-chlorophenyl)-5-nitrobenzoic acid (intermediate 2, step A) (1.05 g, 3.78 mmol) and commercially available 1,1,1-trifluoro-2-methylpropan-2-amine (577 mg, 4.54 mmol).

Step B

3-Amino-5-(4-chlorophenyl)-N-(1,1,1-trifluoro-2-methylpropan-2-yl)-benzamide, light yellow solid (0.57 g, 98%), MS (ISP) m/z=357.1 [(M+H)+], mp 150° C., was prepared in accordance with the general method of intermediate 1, step C, from 3-(4-chlorophenyl)-5-nitro-N-(1,1,1-trifluoro-2-methylpropan-2-yl)-benzamide (0.63 g, 1.63 mmol).

Step C

The title compound, light yellow solid (0.53 g, 71%), MS (ISP) m/z=468.1 [(M+H)+], mp 163° C., was prepared in accordance with the general method of intermediate 1, step D, from 3-Amino-5-(4-chlorophenyl)-N-(1,1,1-trifluoro-2-methylpropan-2-yl)-benzamide (0.56 g, 1.58 mmol).

Intermediate 5: *N*-tert-Butyl-3-(4-fluorophenyl)-5-iodobenzamide

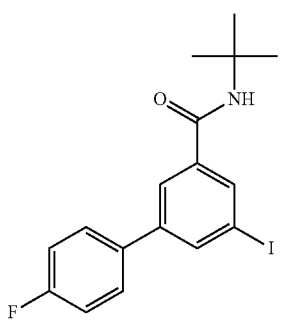 [SMILES: CC(C)(C)NC(=O)c1cc(I)cc(-c2ccc(F)cc2)c1]

Step A 3-(4-Fluorophenyl)-5-nitrobenzoic acid, light brown solid (4.33 g, 97%), MS (ISN) m/z=260.1 [(M−H)−], mp 182° C., was prepared in accordance with the general method of intermediate 1, step B, from commercially available 3-iodo-5-nitrobenzoic acid (5.0 g, 17.1 mmol) and commercially available (4-fluorophenyl)-boronic acid (2.63 g, 18.8 mmol).

Step B

N-tert-Butyl-3-(4-fluorophenyl)-5-nitrobenzamide, yellow solid (1.03 g, 93%), MS (ISP) m/z=317.1 [(M+H)+], mp 180° C., was prepared in accordance with the general method of intermediate 1, step A, from 3-(4-fluorophenyl)-5-nitrobenzoic acid (914 mg, 3.50 mmol) and commercially available 2-methylpropan-2-amine (307 mg, 441 μl, 4.20 mmol).

Step C

3-Amino-N-tert-butyl-5-(4-fluorophenyl)-benzamide, light yellow solid (0.93 g, 99%), MS (ISP) m/z=287.2 [(M+H)+], mp 215° C., was prepared in accordance with the general method of intermediate 1, step C, from N-tert-Butyl-3-(4-fluorophenyl)-5-nitrobenzamide (1.03 g, 3.26 mmol).

Step D

The title compound, off-white (0.83 g, 64%), MS (ISP) m/z=398.1 [(M+H)+], mp 146° C., was prepared in accordance with the general method of intermediate 1, step D, from 3-amino-N-tert-butyl-5-(4-fluorophenyl)-benzamide (0.93 g, 3.25 mmol).

Intermediate 6: 3-Iodo-*N*-(2-methylbutan-2-yl)-5-(4-methylphenyl)-benzamide

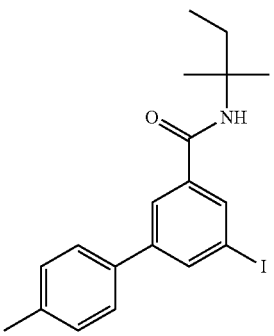 [SMILES: CCC(C)(C)NC(=O)c1cc(I)cc(-c2ccc(C)cc2)c1]

The title compound, light yellow solid (1.69 g, 93%), MS (ISP) m/z=408.2 [(M+H)+], mp 132° C., was prepared in accordance with the general method of intermediate 1, step A, from 3-(4-methylphenyl)-5-iodobenzoic acid [CAS No. 1161830-65-4] (1.50 g, 4.44 mmol) and 2-methylbutan-2-amine (465 mg, 623 μl, 5.33 mmol).

Intermediate 7: *N*-(2-Cyclopropylpropan-2-yl)-3-(4-fluorophenyl)-5-iodobenzamide

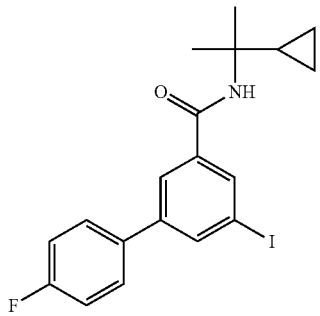 [SMILES: CC(C)(NC(=O)c1cc(I)cc(-c2ccc(F)cc2)c1)C1CC1]

Step A

N-(2-Cyclopropylpropan-2-yl)-3-(4-fluorophenyl)-5-nitrobenzamide, light brown solid (1.05 g, 88%), MS (ISP) m/z=343.1 [(M+H)+], mp 159° C., was prepared in accordance with the general method of intermediate 1, step A, from 3-(4-fluorophenyl)-5-nitrobenzoic acid (intermediate 5, step A) (914 mg, 3.50 mmol) and commercially available 2-cyclopropyl-propan-2-amine hydrochloride (0.57 g, 4.20 mmol).

Step B

3-Amino-N-(2-cyclopropylpropan-2-yl)-5-(4-fluorophenyl)-benzamide, orange semi-solid (0.95 g, 99%), MS (ISP) m/z=313.2 [(M+H)+], was prepared in accordance with the general method of intermediate 1, step C, from N-(2-cyclopropylpropan-2-yl)-3-(4-fluorophenyl)-5-nitrobenzamide (1.05 g, 3.07 mmol).

Step C

The title compound, light orange solid (0.84 g, 66%), MS (ISP) m/z=424.1 [(M+H)+], mp 144° C., was prepared in accordance with the general method of intermediate 1, step D, from 3-amino-N-(2-cyclopropylpropan-2-yl)-5-(4-fluorophenyl)-benzamide (0.94 g, 3.02 mmol).

Intermediate 8: N-tert-Butyl-3-iodo-5-(4-propan-2-ylpyrimidin-5-yl)-benzamide

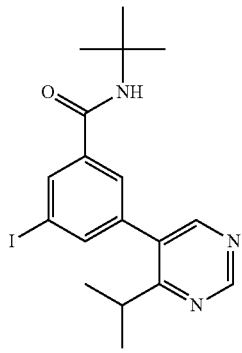 [SMILES: CC(C)c1ncncc1-c1cc(I)cc(C(=O)NC(C)(C)C)c1]

Step A

N-tert-Butyl-3-nitro-5-(4-propan-2-ylpyrimidin-5-yl)-benzamide, light yellow foam (820 mg, 96%), MS (ISP) m/z=343.2 [(M+H)⁺], mp 80° C., was prepared in accordance with the general method of intermediate 1, step B, from N-tert-butyl-3-iodo-5-nitrobenzamide (intermediate 1, step A) (870 mg, 2.5 mmol) and commercially available (4-isopropyl-pyrimidin-5-yl)-boronic acid (539 mg, 3.25 mmol).

Step B

3-Amino-N-tert-butyl-5-(4-propan-2-ylpyrimidin-5-yl)-benzamide, light yellow foam (0.69 g, 93%), MS (ISP) m/z=313.2 [(M+H)⁺], mp 82° C., was prepared in accordance with the general method of intermediate 1, step C, from N-tert-butyl-3-nitro-5-(4-propan-2-ylpyrimidin-5-yl)-benzamide (0.81 g, 2.37 mmol).

Step C

The title compound, off-white foam (0.70 g, 76%), MS (ISP) m/z=424.1 [(M+H)⁺], mp 72° C., was prepared in accordance with the general method of intermediate 1, step D, from 3-amino-N-tert-butyl-5-(4-propan-2-ylpyrimidin-5-yl)-benzamide (0.68 g, 2.18 mmol).

Intermediate 9: N-(2-Cyanopropan-2-yl)-3-iodo-5-(4-propan-2-yl-pyrimidin-5-yl)-benzamide

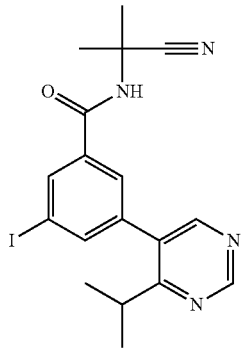 [SMILES: CC(C)c1ncncc1-c1cc(I)cc(C(=O)NC(C)(C)C#N)c1]

Step A

N-(2-Cyanopropan-2-yl)-3-iodo-5-nitrobenzamide, light yellow foam (0.92 g, 73%), MS (ISP) m/z=360.0 [(M+H)⁺], mp 62° C., was prepared in accordance with the general method of intermediate 1, step A, from commercially available 3-iodo-5-nitrobenzoic acid (1.03 g, 3.50 mmol) and commercially available 2-amino-2-methyl-propanenitrile (0.35 g, 4.20 mmol).

Step B

N-(2-Cyanopropan-2-yl)-3-nitro-5-(4-propan-2-yl-pyrimidin-5-yl)-benzamide, light yellow foam (720 mg, 80%), MS (ISP) m/z=354.2 [(M+H)⁺], mp 60° C., was prepared in accordance with the general method of intermediate 1, step B, from N-(2-cyanopropan-2-yl)-3-iodo-5-nitrobenzamide (920 mg, 2.56 mmol) and commercially available (4-isopropyl-pyrimidin-5-yl)-boronic acid (553 mg, 3.33 mmol).

Step C

3-Amino-N-(2-cyanopropan-2-yl)-5-(4-propan-2-yl-pyrimidin-5-yl)-benzamide, off-white solid (0.55 g, 84%), MS (ISP) m/z=324.2 [(M+H)⁺], mp 197° C., was prepared in accordance with the general method of intermediate 1, step C, from N-(2-cyanopropan-2-yl)-3-nitro-5-(4-propan-2-yl-pyrimidin-5-yl)-benzamide (0.72 g, 2.04 mmol).

Step D

The title compound, white foam (0.38 g, 51%), MS (ISP) m/z=435.2 [(M+H)⁺], mp 96° C., was prepared in accordance with the general method of intermediate 1, step D, from 3-amino-N-(2-cyanopropan-2-yl)-5-(4-propan-2-yl-pyrimidin-5-yl)-benzamide (0.55 g, 1.71 mmol).

Intermediate 10: 3-(4-Chlorophenyl)-5-(4-cyclopropyl-pyrimidin-5-yl)-benzoic acid

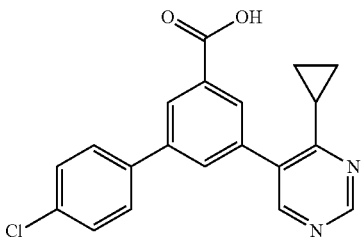 [SMILES: O=C(O)c1cc(-c2ccc(Cl)cc2)cc(-c2cncnc2C2CC2)c1]

Step A

To a stirred solution of commercially available 3-iodo-5-nitrobenzoic acid (3.60 g, 12.3 mmol) and Pd(Ph₃P)₄ (454 mg, 393 µmol) in toluene (68 ml) and ethanol (11.3 ml) was added at room temperature commercially available 4-chloro-phenylboronic acid (2.11 g, 13.5 mmol) and a solution of Cs₂CO₃ (4.40 g, 13.5 mmol) in water (4.56 ml). The reaction mixture was stirred under reflux conditions for 18 h and then cooled to room temperature. To the mixture was added 2N NaOH (50 ml), and the reaction mixture was stirred for 30 min at room temperature. Some precipitated material was collected by filtration. The organic layer was separated, and to the water layer together with the precipitated material was added conc. hydrochloric acid (18 ml) to reach pH<4. The mixture was extracted with ethyl acetate (2×75 ml), the combined organic layers were washed with brine, dried (MgSO₄) and evaporated to yield crude 3-(4-chlorophenyl)-5-nitrobenzoic acid (3.26 g, 11.7 mmol) as brown solid, MS (ISN) m/z=276.1 [(M−H)⁻], which was subsequently dissolved in methanol (29 ml). To the stirred solution was added dropwise thionyl chloride (1.54 g, 0.94 ml, 12.9 mmol) at 0° C. The reaction mixture was allowed to warm to room temperature, and was afterwards stirred under reflux conditions for 2 h. The solvent was removed in vacuo to yield crude methyl 3-(4-chlorophenyl)-5-nitrobenzoate (3.26 g, 11.2 mmol) as a brown solid, MS (ISP) m/z=292.1 [(M+H)⁺], which was subsequently dissolved in methanol (29 ml). To the stirred solution was added at room temperature tin(II)chloride (8.48 g, 44.7 mmol) the reaction mixture was stirred under reflux conditions for 3 h, evaporated, the residue was dissolved in water (150 ml) and basified to pH=9 by addition of Na₂CO₃. The mixture was extracted with dichloro-methane (3×75 ml), the combined organic layers were washed with water (150 ml), brine (150 ml), dried (MgSO₄) and evaporated. The crude product was purified by flash chromatography on silica gel [heptane/ethyl acetate (20-50%)] to yield methyl 3-amino-5-(4-chlorophenyl)-benzoate (2.29 g, 71%) as a yellow solid, MS (ISP) m/z=262.1 [(M+H)⁺], mp 120° C.

Step B

A suspension of methyl 3-amino-5-(4-chlorophenyl)-benzoate (2.45 g, 9.36 mmol), isoamyl nitrite (6.85 g, 7.86 ml, 56.2 mmol), copper(I)iodide (1.78 g, 9.36 mmol) and diiodomethane (15.2 g, 4.58 ml, 56.2 mmol) in THF (24.1 ml) was allowed to stir at room temperature for 1 h hour and afterwards under reflux conditions for 3 h. To the reaction mixture was added toluene (30 ml) at room temperature, the mixture was evaporated and purified by flash chromatography on silica gel [heptane/ethyl acetate (0-50%)] to yield methyl 5-(4-chlorophenyl)-3-iodo-benzoate (3.17 g, 91%) as a light yellow solid, MS (ISP) m/z=372.1 [(M+H)⁺], mp 90.5° C.

Step C 5-(4-Chlorophenyl)-3-iodo-benzoate (3.17 g, 8.51 mmol) was dissolved in DMSO (25.5 ml) at room temperature, and potassium acetate (2.51 g, 25.5 mmol) was added followed by bis(pinacolato)diboron (2.59 g, 10.2 mmol). The reaction mixture was purged with nitrogen in an ultrasonic bath for 5 min, PdCl₂(DPPF)-CH₂Cl₂ adduct (208 mg, 255 μmol) was added and the reaction mixture was allowed to stir at 80° C. for 2.5 h, cooled to room temperature, diluted with water (200 ml) and extracted with diethyl ether (2×120 ml). The combined organic layers were washed with brine (70 ml), dried (MgSO₄) and evaporated. The crude product (4.34 g) was purified by flash chromatography on silica gel [heptane/ethyl acetate (0-50%)] followed by dichloromethane/dichloromethane methanol 9:1 (0-50%)] to yield methyl 3-(4-chlorophenyl)-5-(4,4,5,5-tetramethyl-1,3,2-dioxaborolan-2-yl)-benzoate (2.6 g, 82%) as a white solid, MS (ISP) m/z=373.1 [(M+H)⁺], mp 135° C.

Step D

Methyl 3-(4-chlorophenyl)-5-(4-cyclopropylpyrimidin-5-yl)-benzoate, light yellow oil (0.1 g, 55%), MS (ISP) m/z=365.2 [(M+H)⁺], was prepared in accordance with the general method of example 1 from methyl 3-(4-chlorophenyl)-5-(4,4,5,5-tetramethyl-1,3,2-dioxaborolan-2-yl)-benzoate (186 mg, 0.50 mmol) and commercially available 5-bromo-4-cyclopropyl-pyrimidine (129 mg, 0.65 mmol).

Step E

A mixture of methyl 3-(4-chlorophenyl)-5-(4-cyclopropylpyrimidin-5-yl)-benzoate (90 mg, 247 mol), THF (0.41 ml), MeOH (410 μl), water (410 μl) and lithium hydroxide monohydrate (13.5 mg, 321 μmol) was allowed to stir at room temperature for 3 h. The reaction mixture was concentrated to one third, 2N HCl solution (0.48 ml) was added, the precipitate was collected by filtration, washed with water and dried to yield the title compound (70 mg, 81%) as a light yellow solid, MS (ISP) m/z=351.1 [(M+H)⁺], mp 220.5° C.

Intermediate 11: 3-(4-Chlorophenyl)-5-(4-ethyl-pyrimidin-5-yl)-benzoic acid

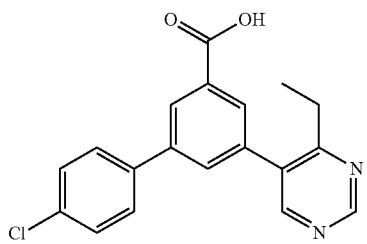 [SMILES: CCc1ncncc1-c1cc(C(=O)O)cc(-c2ccc(Cl)cc2)c1]

The title compound, light yellow solid (130 mg, 77%), MS (ISP) m/z=339.1 [(M+H)⁺], mp 219.5° C., was prepared in accordance with the general method of intermediate 10, steps D and E, from methyl 3-(4-chlorophenyl)-5-(4,4,5,5-tetramethyl-1,3,2-dioxaborolan-2-yl)-benzoate (intermediate 10, step C) (186 mg, 0.50 mmol) and commercially available 5-bromo-4-ethyl-pyrimidine (122 mg, 0.65 mmol)

Intermediate 12: 3-(4-tert-Butyl-pyrimidin-5-yl)-5-(4-chlorophenyl)-benzoic acid

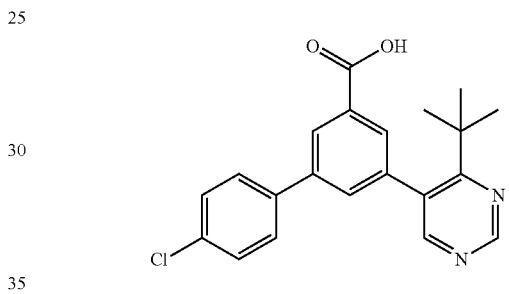

The title compound, white solid (110 mg, 53%), MS (ISP) m/z=367.2 [(M+H)⁺], mp 164.5° C., was prepared in accordance with the general method of intermediate 10, steps D and E, from methyl 3-(4-chlorophenyl)-5-(4,4,5,5-tetramethyl-1,3,2-dioxaborolan-2-yl)-benzoate (intermediate 10, step C) (209 mg, 0.56 mmol) and commercially available 5-bromo-4-(tert-butyl)-pyrimidine (157 mg, 0.73 mmol).

Intermediate 13: N-(1-Hydroxy-2-methyl-propan-2-yl)-3-iodo-5-(4-propan-2-yl-pyrimidin-5-yl)-benzamide

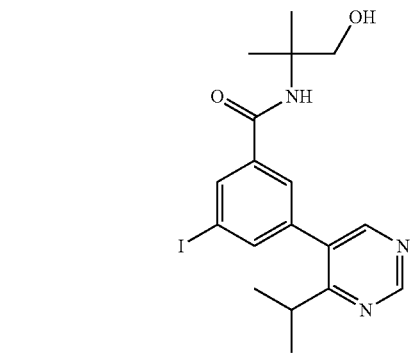 [SMILES: CC(C)c1ncncc1-c1cc(I)cc(C(=O)NC(C)(C)CO)c1]

Step A

N-(1-Hydroxy-2-methylpropan-2-yl)-3-iodo-5-nitrobenzamide, off-white solid (1.18 g, 93%), MS (ISP) m/z=365.1 [(M+H)⁺], mp 166° C., was prepared in accordance with the general method of intermediate 1, step A, from commercially available 3-iodo-5-nitrobenzoic acid (1.03 g, 3.50 mmol) and commercially available 2-amino-2-methylpropan-1-ol (0.37 g, 4.20 mmol).

Step B

N-(1-Hydroxy-2-methylpropan-2-yl)-3-nitro-5-(4-propan-2-yl-pyrimidin-5-yl)-benzamide, yellow semisolid (1.07 g, 92%), MS (ISP) m/z=359.3 [(M+H)⁺], was prepared in accordance with the general method of intermediate 1, step B, from N-(1-hydroxy-2-methylpropan-2-yl)-3-iodo-5-nitrobenzamide (1.18 g, 3.24 mmol) and commercially available (4-isopropyl-pyrimidin-5-yl)-boronic acid (699 mg, 4.21 mmol).

Step C

3-Amino-N-(1-hydroxy-2-methylpropan-2-yl)-5-(4-propan-2-ylpyrimidin-5-yl)benzamide, light yellow semisolid (0.84 g, 86%), MS (ISP) m/z=329.3 [(M+H)⁺], was prepared in accordance with the general method of intermediate 1, step C, from N-(1-hydroxy-2-methylpropan-2-yl)-3-nitro-5-(4-propan-2-yl-pyrimidin-5-yl)-benzamide (1.07 g, 2.99 mmol).

Step D

The title compound, off-white foam (0.43 g, 38%), MS (ISP) m/z=440.2 [(M+H)⁺], mp 61° C., was prepared in accordance with the general method of intermediate 1, step D, from 3-amino-N-(1-hydroxy-2-methylpropan-2-yl)-5-(4-propan-2-ylpyrimidin-5-yl)benzamide (0.84 g, 2.56 mmol).

Intermediate 14: *N*-tert-Butyl-3-(4-chlorophenyl)-5-(4,4,5,5-tetramethyl-1,3,2-dioxaborolan-2-yl)-benzamide

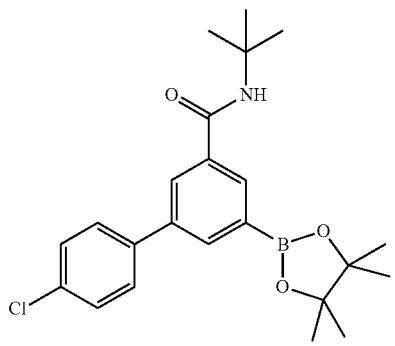 [SMILES: CC(C)(C)NC(=O)c1cc(B2OC(C)(C)C(C)(C)O2)cc(-c2ccc(Cl)cc2)c1]

To a stirred solution of N-tert-butyl-3-(4-chlorophenyl)-5-iodobenzamide (intermediate 1) (207 mg, 0.50 mmol) in DMSO (1.5 ml) was added at room temperature potassium acetate (147 mg, 1.50 mmol) followed by bis(pinacolato) diboron (152 mg, 600 μmol) The reaction mixture was purged with nitrogen in an ultrasonic bath for 5 min, PdCl₂(DPPF)-CH₂Cl₂ adduct (12.2 mg, 15 μmol) was added, and the reaction mixture was allowed to stir for 4.5 h at 80° C., cooled to room temperature, diluted with water (50 ml) and extracted with ethyl acetate (2×100 ml). The combined organic layers were washed with brine (70 ml), dried (MgSO₄) and evaporated. The crude product was purified by flash chromatography on silica gel [heptane/ethyl acetate (0-50%)] to yield the title compound (0.22 g, 94%) as a yellow solid, MS (ISP) m/z=414.3 [(M+H)⁺], mp 162° C.

Intermediate 15: *N*-tert-Butyl-3-(4,4,5,5-tetramethyl-1,3,2-dioxaborolan-2-yl)-5-[4-(trifluorumethyl)-phenyl]-benzamide

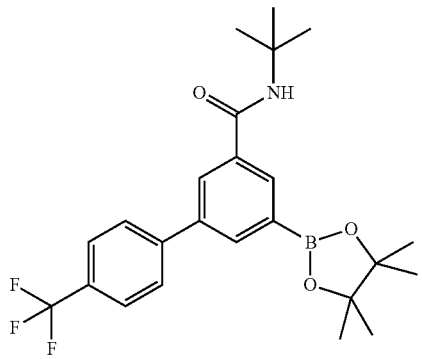 [SMILES: CC(C)(C)NC(=O)c1cc(B2OC(C)(C)C(C)(C)O2)cc(-c2ccc(C(F)(F)F)cc2)c1]

Step A

N-tert-Butyl-3-nitro-5-[4-(trifluoromethyl)-phenyl]-benzamide, light brown solid (0.52 g, 99%), MS (ISP) m/z=367.2 [(M+H)⁺], mp 187.5° C., was prepared in accordance with the general method of intermediate 1, step B, from N-tert-butyl-3-iodo-5-nitrobenzamide (intermediate 1, step A) (0.50 g, 1.44 mmol) and commercially available (4-trifluoromethyl-phenyl)-boronic acid (355 mg, 1.87 mmol).

Step B

3-Amino-N-tert-butyl-5-[4-(trifluoromethyl)-phenyl]-benzamide, light yellow solid (0.48 g, 99%), MS (ISP) m/z=337.2 [(M+H)⁺], mp 228.5° C., was prepared in accordance with the general method of intermediate 1, step C, from N-tert-butyl-3-nitro-5-[4-(trifluoromethyl)-phenyl]-benzamide (0.52 g, 1.42 mmol).

Step C

N-tert-Butyl-3-iodo-5-[4-(trifluoromethyl)-phenyl]-benzamide, light yellow solid (0.44 g, 72%), MS (ISP) m/z=448.1 [(M+H)⁺], mp 139° C., was prepared in accordance with the general method of intermediate 1, step D, from 3-amino-N-tert-butyl-5-[4-(trifluoromethyl)-phenyl]-benzamide (0.46 g, 1.37 mmol).

Step D

The title compound, off-white solid (194 mg, 87%), MS (ISP) m/z=448.4 [(M+H)⁺], mp 219° C., was prepared in accordance with the general method of intermediate 14, from N-tert-butyl-3-iodo-5-[4-(trifluoromethyl)-phenyl]-benzamide (224 mg, 0.5 mmol).

Intermediate 16: *N*-tert-Butyl-3-(3,4-dinuorophenyl)-5-(4,4,5,5-tetramethyl-1,3,2-dioxaborolan-2-yl)-benzamide

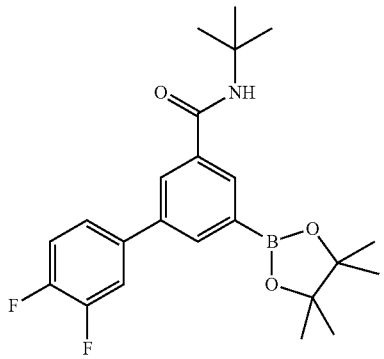 [SMILES: CC(C)(C)NC(=O)c1cc(B2OC(C)(C)C(C)(C)O2)cc(-c2ccc(F)c(F)c2)c1]

Step A

N-tert-Butyl-3-(3,4-difluorophenyl)-5-nitrobenzamide, yellow solid (0.47 g, 98%), MS (ISP) m/z=335.2 [(M+H)+], mp 138° C., was prepared in accordance with the general method of intermediate 1, step B, from N-tert-butyl-3-iodo-5-nitrobenzamide (intermediate 1, step A) (0.50 g, 1.44 mmol) and commercially available (3,4-difluoro-phenyl)-boronic acid (295 mg, 1.87 mmol).

Step B

3-Amino-N-tert-butyl-5-(3,4-difluorophenyl)-benzamide, yellow solid (0.43 g, 99%), MS (ISP) m/z=305.2 [(M+H)+], mp 179° C., was prepared in accordance with the general method of intermediate 1, step C, from N-tert-butyl-3-(3,4-difluorophenyl)-5-nitro-benzamide (0.47 g, 1.43 mmol).

Step C

N-tert-Butyl-3-(3,4-difluorophenyl)-5-iodobenzamide, light yellow foam (0.39 g, 69%), MS (ISP) m/z=416.2 [(M+H)+], mp 139° C., was prepared in accordance with the general method of intermediate 1, step D, from 3-amino-N-tert-butyl-5-(3,4-difluorophenyl)-benzamide (0.43 g, 1.37 mmol).

Step D

The title compound, white solid (238 mg, 61%), MS (ISP) m/z=416.3 [(M+H)+], mp 192° C., was prepared in accordance with the general method of intermediate 14, from N-tert-butyl-3-(3,4-difluorophenyl)-5-iodobenzamide (0.39 g, 0.94 mmol).

Intermediate 17: *N*-tert-Butyl-3-(4-fluorophenyl-5-(4,4,5,5-tetramethyl-1,3,2-dioxaborolan-2-yl)-benzamide

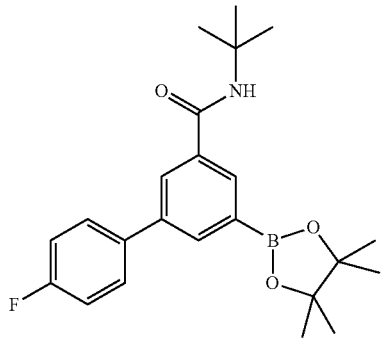 [SMILES: CC(C)(C)NC(=O)c1cc(B2OC(C)(C)C(C)(C)O2)cc(-c2ccc(F)cc2)c1]

The title compound, off-white solid (339 mg, 91%), MS (ISP) m/z=398.3 [(M+H)+], mp 182° C., was prepared in accordance with the general method of intermediate 14, from N-tert-butyl-3-(4-fluorophenyl)-5-iodobenzamide (intermediate 5) (0.37 g, 0.94 mmol).

Example 1

*N*-(2-Methylbutan-2-yl)-3-(4-methylphenyl)-5-pyridin-3-ylbenzamide

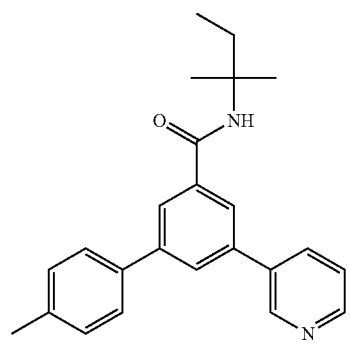 [SMILES: CCC(C)(C)NC(=O)c1cc(-c2ccc(C)cc2)cc(-c2cccnc2)c1]

A mixture of 3-iodo-N-(2-methylbutan-2-yl)-5-(4-methylphenyl)-benzamide (intermediate 6) (102 mg, 0.25 mmol) and commercially available pyridin-3-ylboronic acid (39.9 mg, 325 µmol) in 1,2-dimethoxyethane (1.67 ml) and 2 M Na₂CO₃ solution (416 µl, 832 µmol) was purged with argon in an ultrasonic bath during 5 min at room temperature, triphenyl-phosphine (13.1 mg, 50.0 µmol) and palladium(II) acetate (5.61 mg, 25.0 µmol) were added, and the reaction mixture was allowed to stir for 3 h at 105° C. in a sealed tube. Subsequent purification by flash chromatography on silica gel (ethyl acetate), and a second time on silica gel [dichloromethane/MeOH (0-2%)] yielded the title compound (76 mg, 85%) as a light brown foam, MS (ISP) m/z=359.3 [(M+H)+].

Example 2

N-(2-Methylbutan-2-yl)-3-(4-methylphenyl)-5-pyrimidin-5-ylbenzamide

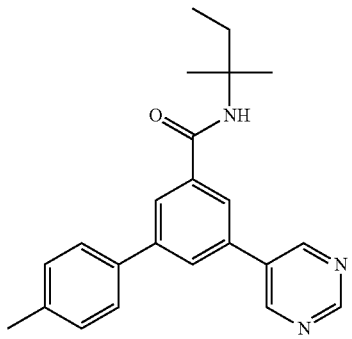 [SMILES: CCC(C)(C)NC(=O)c1cc(-c2ccc(C)cc2)cc(-c2cncnc2)c1]

The title compound, white foam (80 mg, 89%), MS (ISP) m/z=360.3 [(M+H)+], was prepared in accordance with the general method of example 1 from 3-iodo-N-(2-methylbutan-2-yl)-5-(4-methylphenyl)-benzamide (intermediate 6) (102 mg, 0.25 mmol) and commercially available 5-(4,4,5,5-tetramethyl-1,3,2-dioxaborolan-2-yl)-pyrimidine (67.0 mg, 325 µmol).

Example 3

*N*-(2-Methylbutan-2-yl)-3-(4-methylphenyl)-5-(4-propan-2-ylpyrimidin-5-yl)-benzamide

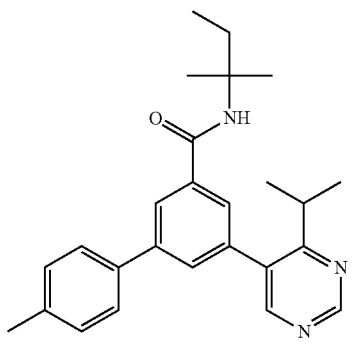 [SMILES: CCC(C)(C)NC(=O)c1cc(-c2ccc(C)cc2)cc(-c2cncnc2C(C)C)c1]

The title compound, white foam (79 mg, 79%), MS (ISP) m/z=402.2 [(M+H)⁺], was prepared in accordance with the general method of example 1 from 3-iodo-N-(2-methylbutan-2-yl)-5-(4-methylphenyl)-benzamide (intermediate 6) (102 mg, 0.25 mmol) and commercially available (4-isopropylpyrimidin-5-yl)-boronic acid (53.9 mg, 325 µmol).

Example 4

N-(2-Methylbutan-2-yl)-3-(4-methylphenyl)-5-(4-methylpyridin-3-yl)-benzamide

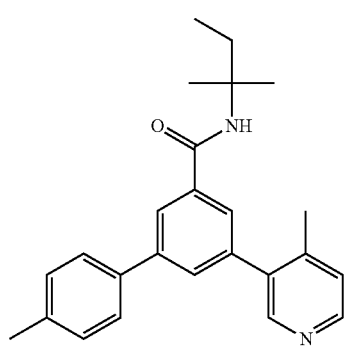

The title compound, white foam (26 mg, 28%), MS (ISP) m/z=373.3 [(M+H)⁺], was prepared in accordance with the general method of example 1 from 3-iodo-N-(2-methylbutan-2-yl)-5-(4-methylphenyl)-benzamide (intermediate 6) (102 mg, 0.25 mmol) and commercially available (4-methylpyridin-3-yl)-boronic acid (44.5 mg, 325 µmol).

Example 5

N-(2-Methylbutan-2-yl)-3-(4-methylphenyl)-5-(2-methylpyridin-3-yl)-benzamide

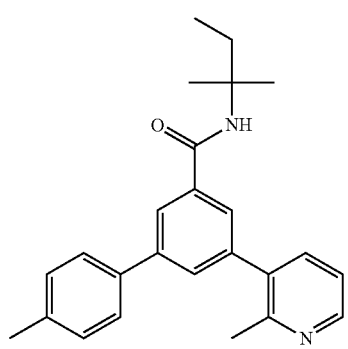 [SMILES: CCC(C)(C)NC(=O)c1cc(-c2ccc(C)cc2)cc(-c2cccnc2C)c1]

The title compound, light yellow foam (67 mg, 72%), MS (ISP) m/z=373.3 [(M+H)⁺], was prepared in accordance with the general method of example 1 from 3-iodo-N-(2-methylbutan-2-yl)-5-(4-methylphenyl)-benzamide (intermediate 6) (102 mg, 0.25 mmol) and commercially available (2-methylpyridin-3-yl)-boronic acid (44.5 mg, 325 µmol).

Example 6

N-(2-Methylbutan-2-yl)-3-(4-methylphenyl)-5-(4-propan-2-ylpyridin-3-yl)-benzamide

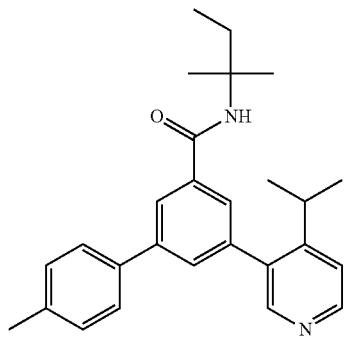 [SMILES: CCC(C)(C)NC(=O)c1cc(-c2ccc(C)cc2)cc(-c2cnccc2C(C)C)c1]

The title compound, light brown foam (78 mg, 78%), MS (ISP) m/z=401.3 [(M+H)⁺], was prepared in accordance with the general method of example 1 from 3-iodo-N-(2-methylbutan-2-yl)-5-(4-methylphenyl)-benzamide (intermediate 6) (102 mg, 0.25 mmol) and commercially available (4-isopropylpyridin-3-yl)-boronic acid (53.6 mg, 325 µmol).

Example 7

N-tert-Butyl-3-(4-chlorophenyl)-5-(4-methylpyridin-3-yl)-benzamide

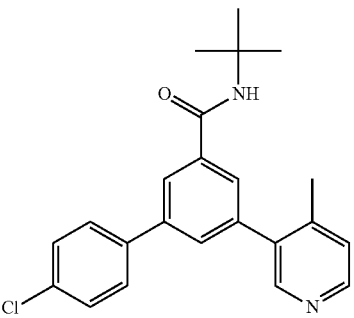 [SMILES: Cc1ccncc1-c1cc(C(=O)NC(C)(C)C)cc(-c2ccc(Cl)cc2)c1]

The title compound, light brown foam (10 mg, 11%), MS (ISP) m/z=379.2 [(M+H)⁺], was prepared in accordance with the general method of example 1 from N-tert-butyl-3-(4-chlorophenyl)-5-iodobenzamide (intermediate 1) (103 mg, 0.25 mmol) and commercially available (4-methylpyridin-3-yl)-boronic acid (44.5 mg, 325 µmol).

Example 8

N-tert-Butyl-3-(4-chlorophenyl)-5-pyridin-3-ylbenzamide

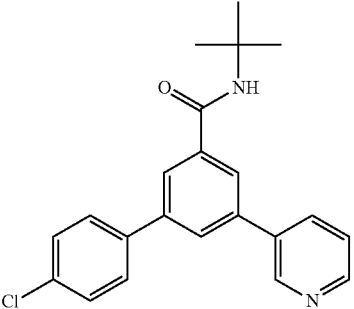

The title compound, white solid (55 mg, 60%), MS (ISP) m/z=365.2 [(M+H)⁺], mp 177° C., was prepared in accordance with the general method of example 1 from N-tert-butyl-3-(4-chlorophenyl)-5-iodobenzamide (intermediate 1) (103 mg, 0.25 mmol) and commercially available pyridin-3-ylboronic acid (39.9 mg, 325 µmol).

Example 9

N-tert-Butyl-3-(4-chlorophenyl)-5-(4-propan-2-ylpyridin-3-yl)-benzamide

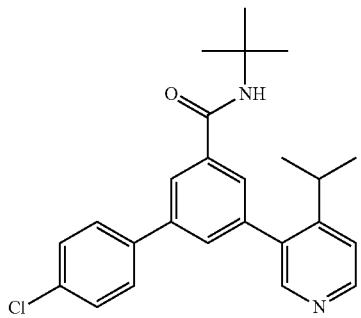

The title compound, white solid (66 mg, 65%), MS (ISP) m/z=407.3 [(M+H)⁺], mp 148° C., was prepared in accordance with the general method of example 1 from N-tert-butyl-3-(4-chlorophenyl)-5-iodobenzamide (intermediate 1) (103 mg, 0.25 mmol) and commercially available (4-isopropylpyridin-3-yl)-boronic acid (53.6 mg, 325 µmol).

Example 10

N-tert-Butyl-3-(4-chlorophenyl)-5-pyrimidin-5-ylbenzamide

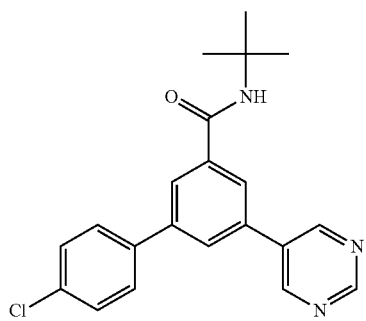 [SMILES: CC(C)(C)NC(=O)c1cc(-c2ccc(Cl)cc2)cc(-c2cncnc2)c1]

The title compound, white solid (50 mg, 55%), MS (ISP) m/z=366.2 [(M+H)⁺], mp 195° C., was prepared in accordance with the general method of example 1 from N-tert-butyl-3-(4-chlorophenyl)-5-iodobenzamide (intermediate 1) (103 mg, 0.25 mmol) and commercially available pyrimidin-5-ylboronic acid (40.3 mg, 325 µmol).

Example 11

N-tert-Butyl-3-(4-chlorophenyl)-5-(4-propan-2-ylpyrimidin-5-yl)-benzamide

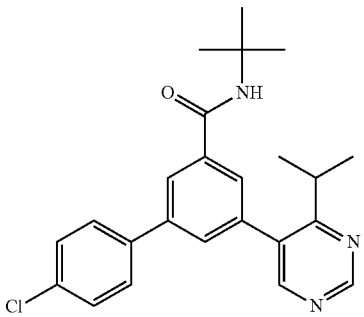 [SMILES: CC(C)c1ncncc1-c1cc(C(=O)NC(C)(C)C)cc(-c2ccc(Cl)cc2)c1]

The title compound, white solid (64 mg, 63%), MS (ISP) m/z=408.3 [(M+H)⁺], mp 182° C., was prepared in accordance with the general method of example 1 from N-tert-butyl-3-(4-chlorophenyl)-5-iodobenzamide (intermediate 1) (103 mg, 0.25 mmol) and commercially available (4-isopropylpyrimidin-5-yl)-boronic acid (53.9 mg, 325 µmol).

Example 12

(RS)-3-(4-Chlorophenyl)-N-(3-methyl-1,1-dioxothiolan-3-yl)-5-(4-propan-2-ylpyrimidin-5-yl)-benzamide

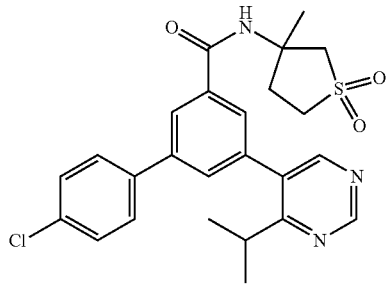 [SMILES: CC(C)c1ncncc1-c1cc(C(=O)NC2(C)CCS(=O)(=O)C2)cc(-c2ccc(Cl)cc2)c1]

The title compound, light yellow foam (102 mg, 84%), MS (ISP) m/z=484.3 [(M+H)⁺], was prepared in accordance with the general method of example 1 from (RS)-3-(4-chlorophenyl)-5-iodo-N-(3-methyl-1,1-dioxothiolan-3-yl)-benzamide (intermediate 2) (122 mg, 0.25 mmol) and commercially available (4-isopropylpyrimidin-5-yl)-boronic acid (53.9 mg, 325 µmol).

Example 13

(RS)-3-(4-Chlorophenyl)-N-(3-methyl-1,1-dioxothiolan-3-yl)-5-(2-methyl-pyridin-3-yl)-benzamide

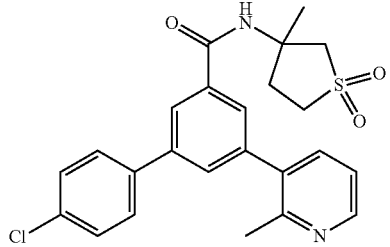 [SMILES: Cc1ncccc1-c1cc(C(=O)NC2(C)CCS(=O)(=O)C2)cc(-c2ccc(Cl)cc2)c1]

The title compound, white foam (35 mg, 31%), MS (ISP) m/z=455.3 [(M+H)⁺], was prepared in accordance with the general method of example 1 from (RS)-3-(4-chlorophenyl)-5-iodo-N-(3-methyl-1,1-dioxothiolan-3-yl)-benzamide (intermediate 2) (122 mg, 0.25 mmol) and commercially available (2-methylpyridin-3-yl)-boronic acid (44.5 mg, 325 µmol).

Example 14

N-(2-Methylbutan-2-yl)-3-(4-methylphenyl)-5-(2-propan-2-ylpyridin-3-yl)-benzamide

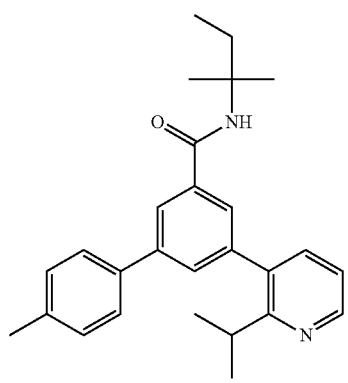 [SMILES: CCC(C)(C)NC(=O)c1cc(-c2ccc(C)cc2)cc(-c2cccnc2C(C)C)c1]

The title compound, light brown foam (84 mg, 84%), MS (ISP) m/z=401.4 [(M+H)⁺], was prepared in accordance with the general method of example 1 from 3-iodo-N-(2-methylbutan-2-yl)-5-(4-methylphenyl)-benzamide (intermediate 6) (102 mg, 0.25 mmol) and commercially available (2-isopropylpyridin-3-yl)-boronic acid (53.6 mg, 325 µmol).

Example 15

N-tert-Butyl-3-(4-chlorophenyl)-5-(2-propan-2-ylpyridin-3-yl)-benzamide

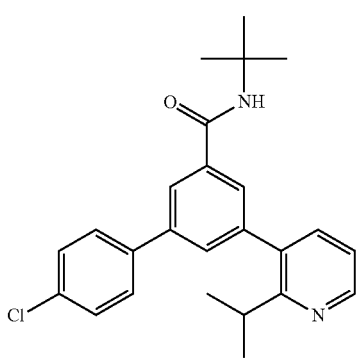 [SMILES: CC(C)c1ncccc1-c1cc(C(=O)NC(C)(C)C)cc(-c2ccc(Cl)cc2)c1]

The title compound, light yellow foam (93 mg, 91%), MS (ISP) m/z=407.3 [(M+H)⁺], was prepared in accordance with the general method of example 1 from N-tert-butyl-3-(4-chlorophenyl)-5-iodobenzamide (intermediate 1) (103 mg, 0.25 mmol) and commercially available (2-isopropylpyridin-3-yl)-boronic acid (53.6 mg, 325 µmol).

Example 16

3-(4-Chlorophenyl)-N-(2-cyclopropylpropan-2-yl)-5-(4-propan-2-ylpyrimidin-5-yl)-benzamide

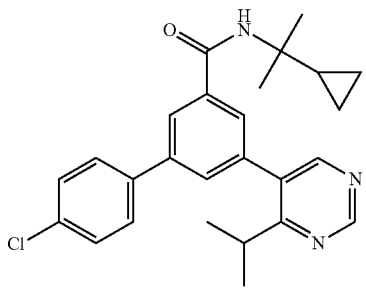 [SMILES: CC(C)c1ncncc1-c1cc(C(=O)NC(C)(C)C2CC2)cc(-c2ccc(Cl)cc2)c1]

The title compound, light brown foam (86 mg, 79%), MS (ISP) m/z=434.3 [(M+H)⁺], was prepared in accordance with the general method of example 1 from 3-(4-chlorophenyl)-N-(2-cyclopropylpropan-2-yl)-5-iodobenzamide (intermediate 3) (110 mg, 0.25 mmol) and commercially available (4-isopropylpyrimidin-5-yl)-boronic acid (53.9 mg, 325 µmol).

Example 17

3-(4-Chlorophenyl)-N-(2-cyclopropylpropan-2-yl)-5-(2-methylpyridin-3-yl)-benzamide

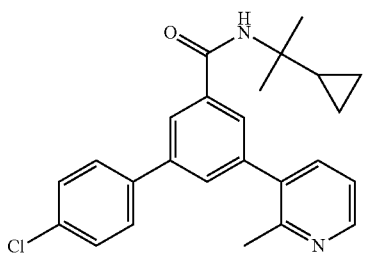 [SMILES: Cc1ncccc1-c1cc(C(=O)NC(C)(C)C2CC2)cc(-c2ccc(Cl)cc2)c1]

The title compound, light yellow foam (55 mg, 54%), MS (ISP) m/z=405.2 [(M+H)⁺], was prepared in accordance with the general method of example 1 from 3-(4-chlorophenyl)-N-(2-cyclopropylpropan-2-yl)-5-iodobenzamide (intermediate 3) (110 mg, 0.25 mmol) and commercially available (2-methylpyridin-3-yl)-boronic acid (44.5 mg, 325 µmol).

Example 18

3-(4-Chlorophenyl)-5-(4-propan-2-ylpyrimidin-5-yl)-N-(1,1,1-trifluoro-2-methylpropan-2-yl)-benzamide

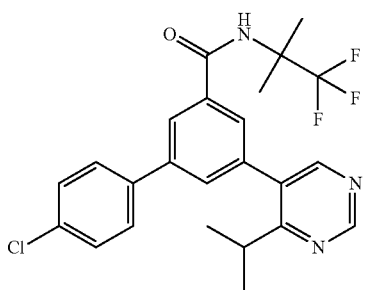 [SMILES: CC(C)c1ncncc1-c1cc(C(=O)NC(C)(C)C(F)(F)F)cc(-c2ccc(Cl)cc2)c1]

The title compound, light yellow solid (92 mg, 80%), MS (ISP) m/z=462.3 [(M+H)⁺], mp 170° C., was prepared in accordance with the general method of example 1 from 3-(4-chlorophenyl)-5-iodo-N-(1,1,1-trifluoro-2-methylpropan-2-yl)-benzamide (intermediate 4) (117 mg, 0.25 mmol) and commercially available (4-isopropylpyrimidin-5-yl)-boronic acid (53.9 mg, 325 μmol).

Example 19

3-(4-Chlorophenyl)-5-(2-methylpyridin-3-yl)-*N*-( 1,1,1-trifluoro-2-methylpropan-2-yl)-benzamide

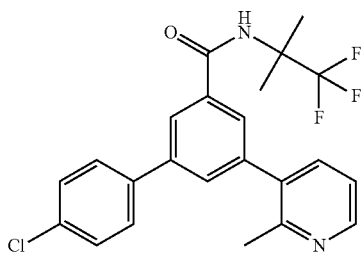 [SMILES: Cc1ncccc1-c1cc(C(=O)NC(C)(C)C(F)(F)F)cc(-c2ccc(Cl)cc2)c1]

The title compound, white foam (72 mg, 67%), MS (ISP) m/z=433.2 [(M+H)⁺], was prepared in accordance with the general method of example 1 from 3-(4-chlorophenyl)-5-iodo-N-(1,1,1-trifluoro-2-methylpropan-2-yl)-benzamide (intermediate 4) (117 mg, 0.25 mmol) and commercially available (2-methylpyridin-3-yl)-boronic acid (44.5 mg, 325 μmol).

Example 20

*N*-terl-Butyl-3-(4-fluorophenyl)-5-(4-propan-2-ylpyrimidin-5-yl)-benzamide

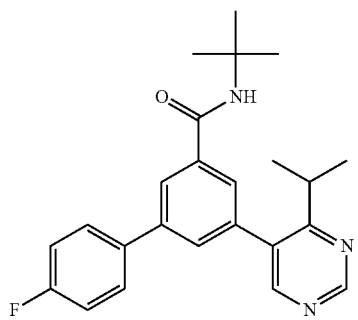 [SMILES: CC(C)c1ncncc1-c1cc(C(=O)NC(C)(C)C)cc(-c2ccc(F)cc2)c1]

The title compound, light yellow foam (90 mg, 92%), MS (ISP) m/z=392.3 [(M+H)⁺], mp 79° C., was prepared in accordance with the general method of example 1 from N-tert-butyl-3-(4-fluorophenyl)-5-iodobenzamide (intermediate 5) (99.3 mg, 0.25 mmol) and commercially available (4-isopropylpyrimidin-5-yl)-boronic acid (53.9 mg, 325 μmol).

Example 21

*N*-tert-Butyl-3-(4-fluorophenyl)-5-(4-methylpyridin-3-yl)-benzamide

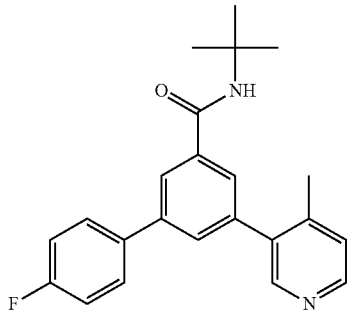 [SMILES: Cc1ccncc1-c1cc(C(=O)NC(C)(C)C)cc(-c2ccc(F)cc2)c1]

The title compound, light yellow foam (30 mg, 33%), MS (ISP) m/z=363.2 [(M+H)⁺], mp 83° C., was prepared in accordance with the general method of example 1 from N-tert-butyl-3-(4-fluorophenyl)-5-iodobenzamide (intermediate 5) (99.3 mg, 0.25 mmol) and commercially available (4-methylpyridin-3-yl)-boronic acid (44.5 mg, 325 μmol).

Example 22

N-(2-Cydopropylpropan-2-yl)-3-(4-fluorophenyl)-5-(4-propan-2-ylpyrimidin-5-yl)benzamide

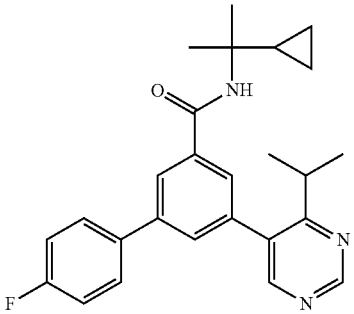 [SMILES: CC(C)c1ncncc1-c1cc(C(=O)NC(C)(C)C2CC2)cc(-c2ccc(F)cc2)c1]

The title compound, white foam (80 mg, 77%), MS (ISP) m/z=418.2 [(M+H)⁺], mp 74° C., was prepared in accordance with the general method of example 1 from N-(2-cyclopropylpropan-2-yl)-3-(4-fluorophenyl)-5-iodobenzamide (intermediate 7) (106 mg, 0.25 mmol) and commercially available (4-isopropylpyrimidin-5-yl)-boronic acid (53.9 mg, 325 μmol).

Example 23

*N*-(2-Cyclopropylpropan-2-yl)-3-(4-fluorophenyl)-5-(4-methylpyridin-3-yl)-benzamide

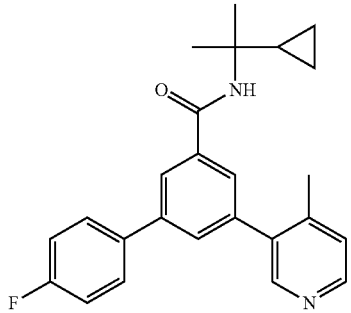 [SMILES: Cc1ccncc1-c1cc(C(=O)NC(C)(C)C2CC2)cc(-c2ccc(F)cc2)c1]

The title compound, white foam (35 mg, 36%), MS (ISP) m/z=389.2 [(M+H)+], mp 76° C., was prepared in accordance with the general method of example 1 from N-(2-cyclopropylpropan-2-yl)-3-(4-fluorophenyl)-5-iodobenzamide (intermediate 7) (106 mg, 0.25 mmol) and commercially available (4-methylpyridin-3-yl)-boronic acid (44.5 mg, 325 μmol).

Example 24

N-tert-Butyl-3-(4-fluorophenyl)-5-(2-methylpyridin-3-yl)-benzamide

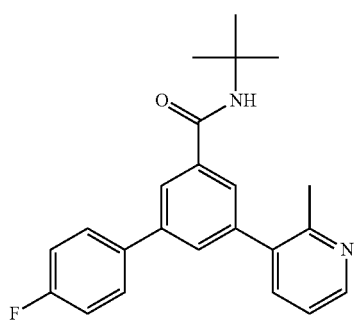 [SMILES: Cc1ncccc1-c1cc(C(=O)NC(C)(C)C)cc(-c2ccc(F)cc2)c1]

The title compound, white foam (63 mg, 70%), MS (ISP) m/z=363.2 [(M+H)+], mp 78° C., was prepared in accordance with the general method of example 1 from N-tert-butyl-3-(4-fluorophenyl)-5-iodobenzamide (intermediate 5) (99.3 mg, 0.25 mmol) and commercially available 2-methyl-3-(4,4,5,5-tetramethyl-1,3,2-dioxaborolan-2-yl)-pyridine (71.2 mg, 325 μmol).

Example 25

N-tert-Butyl-3-(4-methylplenyl)-5-(4-propan-2-ylpyrimidin-5-yl)-benzamide

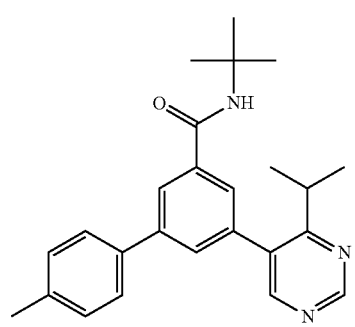 [SMILES: Cc1ccc(-c2cc(C(=O)NC(C)(C)C)cc(-c3cncnc3C(C)C)c2)cc1]

The title compound, light yellow foam (47 mg, 49%), MS (ISP) m/z=388.2 [(M+H)+], mp 91° C., was prepared in accordance with the general method of example 1 from N-tert-butyl-3-iodo-5-(4-propan-2-ylpyrimidin-5-yl)-benzamide (intermediate 8) (106 mg, 0.25 mmol) and commercially available p-tolylboronic acid (44.2 mg, 325 μmol).

Example 26

N-tert-Butyl-3-(3,4-difluorophenyl)-5-(4-propan-2-ylpyrimidin-5-yl)-benzamide

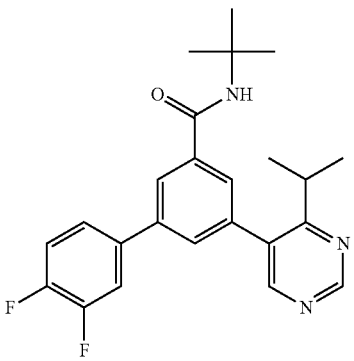 [SMILES: CC(C)c1ncncc1-c1cc(C(=O)NC(C)(C)C)cc(-c2ccc(F)c(F)c2)c1]

The title compound, white foam (91 mg, 89%), MS (ISP) m/z=410.2 [(M+H)+], mp 80° C., was prepared in accordance with the general method of example 1 from N-tert-butyl-3-iodo-5-(4-propan-2-ylpyrimidin-5-yl)-benzamide (intermediate 8) (106 mg, 0.25 mmol) and commercially available (3,4-difluorophenyl)-boronic acid (51.3 mg, 325 μmol).

Example 27

N-tert-Butyl-3-(4-cyclopropylphenyl)-5-(4-propan-2-ylpyrimidin-5-yl)-benzamide

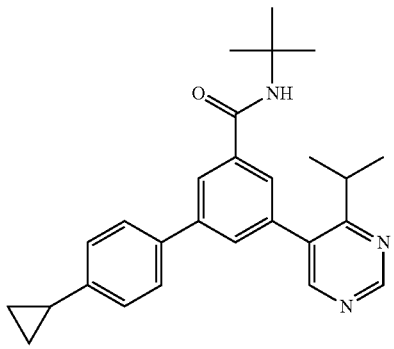 [SMILES: CC(C)c1ncncc1-c1cc(C(=O)NC(C)(C)C)cc(-c2ccc(C3CC3)cc2)c1]

The title compound, white foam (76 mg, 74%), MS (ISP) m/z=414.3 [(M+H)+], mp 91.5° C., was prepared in accordance with the general method of example 1 from N-tert-butyl-3-iodo-5-(4-propan-2-ylpyrimidin-5-yl)-benzamide (intermediate 8) (106 mg, 0.25 mmol) and commercially available (4-cyclopropylphenyl)-boronic acid (52.6 mg, 325 μmol).

Example 28

N-tert-Butyl-3-(4-propan-2-ylpyrimidin-5-yl)-5-[4-(trifluoromethyl)-phenyl]-benzamide

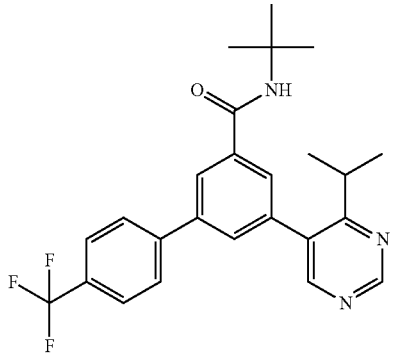 [SMILES: CC(C)c1ncncc1-c1cc(C(=O)NC(C)(C)C)cc(-c2ccc(C(F)(F)F)cc2)c1]

The title compound, light yellow solid (91 mg, 82%), MS (ISP) m/z=442.3 [(M+H)⁺], mp 168° C., was prepared in accordance with the general method of example 1 from N-tert-butyl-3-iodo-5-(4-propan-2-ylpyrimidin-5-yl)-benzamide (intermediate 8) (106 mg, 0.25 mmol) and commercially available (4-trifluoromethylphenyl)-boronic acid (61.7 mg, 325 μmol).

Example 29

N-tert-Butyl-3-(4-fluoro-3-methylphenyl)-5-(4-propan-2ylpyrimidin-5-yl)-benzamide

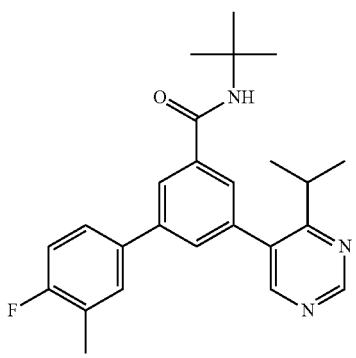 [SMILES: Cc1cc(-c2cc(C(=O)NC(C)(C)C)cc(-c3cncnc3C(C)C)c2)ccc1F]

The title compound, off-white foam (72 mg, 71%), MS (ISP) m/z=406.3 [(M+H)⁺], mp 83° C., was prepared in accordance with the general method of example 1 from N-tert-butyl-3-iodo-5-(4-propan-2-ylpyrimidin-5-yl)-benzamide (intermediate 8) (106 mg, 0.25 mmol) and commercially available (4-fluoro-3-methylphenyl)-boronic acid (50.0 mg, 325 μmol).

Example 30

N-tert-Butyl-3-(3-fluoro-4-methylphenyl)-5-(4-propan-2-ylpyrimidin-5-yl)-benzamide

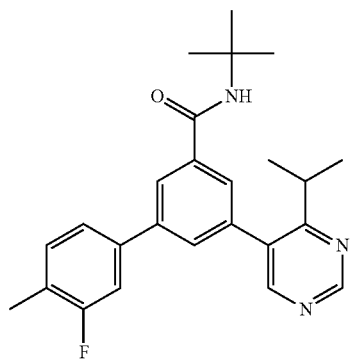

The title compound, off-white foam (94 mg, 93%), MS (ISP) m/z=406.3 [(M+H)⁺], mp 90° C., was prepared in accordance with the general method of example 1 from N-tert-butyl-3-iodo-5-(4-propan-2-ylpyrimidin-5-yl)-benzamide (intermediate 8) (106 mg, 0.25 mmol) and commercially available (3-fluoro-4-methylphenyl)-boronic acid (50.0 mg, 325 μmol).

Example 31

N-tert-Butyl-3-(4-chloro-3-fluorophenyl)-5-(4-propan-2-ylpyrimidin-5-yl)-benzamide

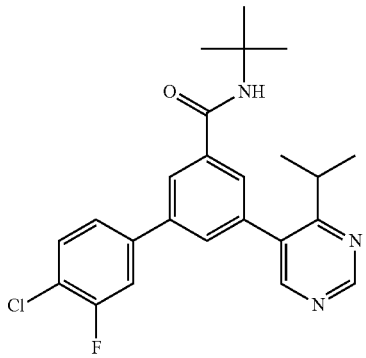 [SMILES: CC(C)c1ncncc1-c1cc(C(=O)NC(C)(C)C)cc(-c2ccc(Cl)c(F)c2)c1]

The title compound, white foam (88 mg, 83%), MS (ISP) m/z=426.3 [(M+H)⁺], mp 93° C., was prepared in accordance with the general method of example 1 from N-tert-butyl-3-iodo-5-(4-propan-2-ylpyrimidin-5-yl)-benzamide (intermediate 8) (106 mg, 0.25 mmol) and commercially available (4-chloro-3-fluorophenyl)-boronic acid (56.7 mg, 325 μmol).

Example 32

N-tert-Butyl-3-(4-cyanophenyl)-5-(4-propan-2-ylpyrimidin-5-yl)-benzamide

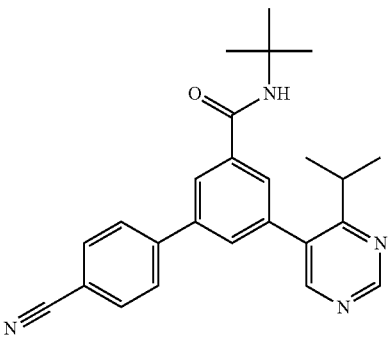 [SMILES: CC(C)c1ncncc1-c1cc(C(=O)NC(C)(C)C)cc(-c2ccc(C#N)cc2)c1]

The title compound, white foam (90 mg, 90%), MS (ISP) m/z=399.3 [(M+H)⁺], mp 98° C., was prepared in accordance with the general method of example 1 from N-tert-butyl-3-iodo-5-(4-propan-2-ylpyrimidin-5-yl)-benzamide (intermediate 8) (106 mg, 0.25 mmol) and commercially available (4-cyanophenyl)-boronic acid (47.8 mg, 325 μmol).

Example 33

N-tert-Butyl-3-(4-methoxyphenyl)-5-(4-propan-2-ylpyrimidin-5-yl)-benzamide

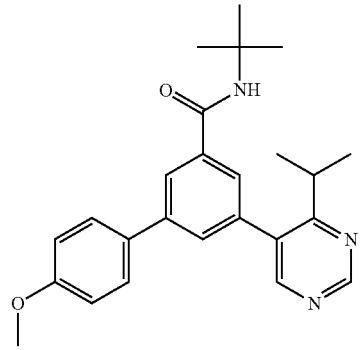 [SMILES: COc1ccc(-c2cc(C(=O)NC(C)(C)C)cc(-c3cncnc3C(C)C)c2)cc1]

The title compound, off-white foam (81 mg, 80%), MS (ISP) m/z=404.3 [(M+H)+], mp 84° C., was prepared in accordance with the general method of example 1 from N-tert-butyl-3-iodo-5-(4-propan-2-ylpyrimidin-5-yl)-benzamide (intermediate 8) (106 mg, 0.25 mmol) and commercially available (4-methoxyphenyl)-boronic acid (49.4 mg, 325 μmol).

Example 34

*N*-(2-Cyanopropan-2-yl)-3-(3-fluoro-4-methylphtmyl)-5-(4-propan-2-yl-pyrimidin-5-yl)-benzamide

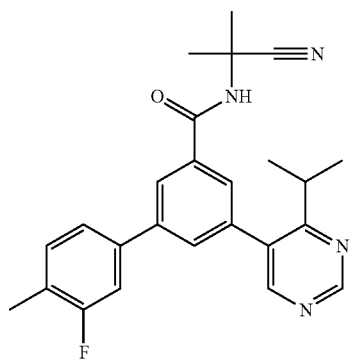 [SMILES: Cc1ccc(-c2cc(C(=O)NC(C)(C)C#N)cc(-c3cncnc3C(C)C)c2)cc1F]

The title compound, white foam (44 mg, 42%), MS (ISP) m/z=417.3 [(M+H)+], mp 102.5° C., was prepared in accordance with the general method of example 1 from N-(2-cyanopropan-2-yl)-3-iodo-5-(4-propan-2-yl-pyrimidin-5-yl)-benzamide (intermediate 9) (109 mg, 0.25 mmol) and commercially available (3-fluoro-4-methylphenyl)-boronic acid (50.0 mg, 325 μmol).

Example 35

*N*-(2-Cyanopropan-2-yl)-3-(4-fluoro-3-methylphenyl-5-(4-propan-2-yl-pyrimidin-5-yl)-benzamide

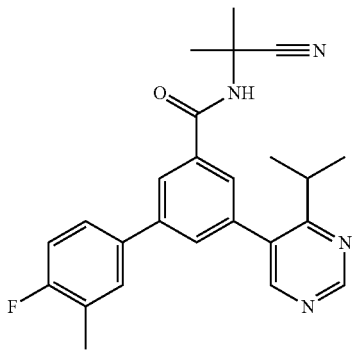 [SMILES: Cc1cc(-c2cc(C(=O)NC(C)(C)C#N)cc(-c3cncnc3C(C)C)c2)ccc1F]

The title compound, white foam (44 mg, 42%), MS (ISP) m/z=417.3 [(M+H)+], mp 101° C., was prepared in accordance with the general method of example 1 from N-(2-cyanopropan-2-yl)-3-iodo-5-(4-propan-2-yl-pyrimidin-5-yl)-benzamide (intermediate 9) (109 mg, 0.25 mmol) and commercially available (4-fluoro-3-methylphenyl)-boronic acid (50.0 mg, 325 μmol).

Example 36

*N*-Cyanopropan-2-yl)-3-(4-fluorophenyl)-5-(4-propan-2-yl-pyrimidin-5-yl)-benzamide

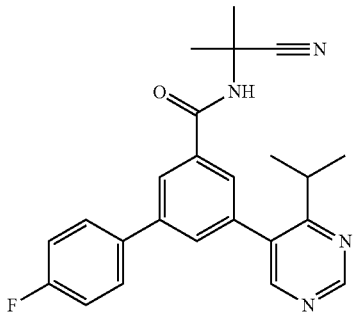 [SMILES: CC(C)c1ncncc1-c1cc(C(=O)NC(C)(C)C#N)cc(-c2ccc(F)cc2)c1]

The title compound, white foam (43 mg, 43%), MS (ISP) m/z=403.3 [(M+H)+], mp 97° C., was prepared in accordance with the general method of example 1 from N-(2-cyanopropan-2-yl)-3-iodo-5-(4-propan-2-yl-pyrimidin-5-yl)-benzamide (intermediate 9) (109 mg, 0.25 mmol) and commercially available (4-fluorophenyl)-boronic acid (45.5 mg, 325 μmol).

Example 37

*N*-(2-Cyanopropan-2-yl)-3-(4-propan-2-yl-pyrimidin-5-yl)-5-[4-(trinuoromethyl)-phenyl]-benzamide

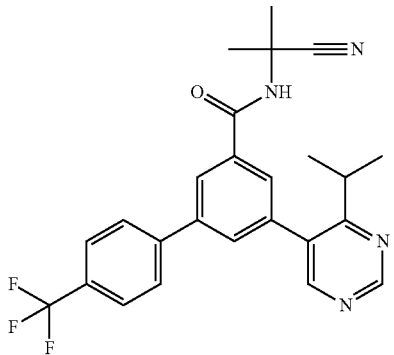 [SMILES: CC(C)c1ncncc1-c1cc(C(=O)NC(C)(C)C#N)cc(-c2ccc(C(F)(F)F)cc2)c1]

The title compound, light yellow foam (45 mg, 40%), MS (ISP) m/z=453.3 [(M+H)+], mp 98° C., was prepared in accordance with the general method of example 1 from N-(2-cyanopropan-2-yl)-3-iodo-5-(4-propan-2-yl-pyrimidin-5-yl)-benzamide (intermediate 9) (109 mg, 0.25 mmol) and commercially available (4-trifluoromethylphenyl)-boronic acid (61.7 mg, 325 μmol).

Example 38

3-(4-Chlorophtnyl)-*N*-(2-cyanopropan-2-yl)-5-(4-propan-2-yl-pyrimidin-5-yl)-benzamide

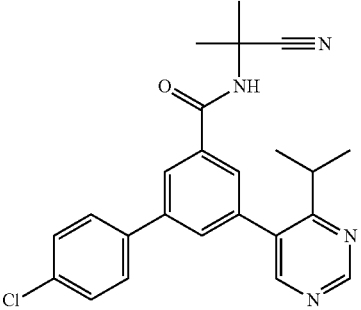 [SMILES: CC(C)c1ncncc1-c1cc(C(=O)NC(C)(C)C#N)cc(-c2ccc(Cl)cc2)c1]

The title compound, white foam (41 mg, 39%), MS (ISP) m/z=419.3 [(M+H)⁺], mp 97° C., was prepared in accordance with the general method of example 1 from N-(2-cyanopropan-2-yl)-3-iodo-5-(4-propan-2-yl-pyrimidin-5-yl)-benzamide (intermediate 9) (109 mg, 0.25 mmol) and commercially available (4-chlorophenyl)-boronic acid (50.8 mg, 325 μmol).

Example 39

*N*-tert-Butyl-3-(4-chlurophenyl)-5-(4-cyclopropyl-pyrimidin-5-yl)-benzamide

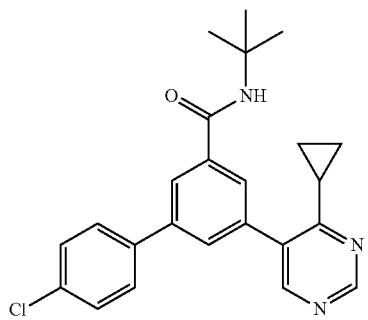 [SMILES: CC(C)(C)NC(=O)c1cc(-c2ccc(Cl)cc2)cc(-c2cncnc2C2CC2)c1]

The title compound, white foam (60 mg, 74%), MS (ISP) m/z=406.3 [(M+H)⁺], mp 96° C., was prepared in accordance with the general method of intermediate 1, step A, from 3-(4-chlorophenyl)-5-(4-cyclopropyl-pyrimidin-5-yl)-benzoic acid (intermediate 10) (70 mg, 0.20 mmol) and commercially available 2-methylpropan-2-amine (17.9 mg, 0.24 mmol).

Example 40

*N*-tert-Butyl-3-(4-chlorophenyl)-5-(4-ethyl-pyrimidin-5-yl)-benzamide

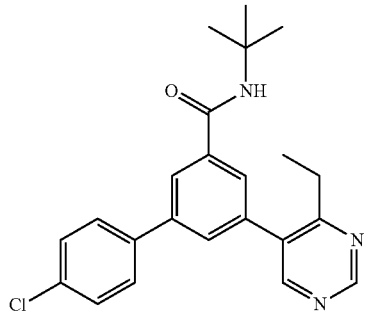 [SMILES: CCc1ncncc1-c1cc(C(=O)NC(C)(C)C)cc(-c2ccc(Cl)cc2)c1]

The title compound, white foam (100 mg, 72%), MS (ISP) m/z=394.3 [(M+H)⁺], mp 75° C., was prepared in accordance with the general method of intermediate 1, step A, from 3-(4-chlorophenyl)-5-(4-cyclopropyl-pyrimidin-5-yl)-benzoic acid (intermediate 10) (120 mg, 0.35 mmol) and commercially available 2-methylpropan-2-amine (31.7 mg, 0.43 mmol).

Example 41

*N*-tert-Butyl-3-(4-chlorophenyl)-5-(4-methyl-pyrimidin-5-yl)-benzamide

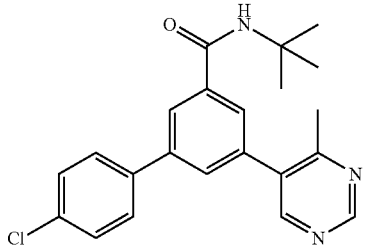 [SMILES: Cc1ncncc1-c1cc(C(=O)NC(C)(C)C)cc(-c2ccc(Cl)cc2)c1]

The title compound, off-white foam (50 mg, 53%), MS (ISP) m/z=380.3 [(M+H)⁺], mp 192° C., was prepared in accordance with the general method of example 1 from N-tert-butyl-3-(4-chlorophenyl)-5-(4,4,5,5-tetramethyl-1,3,2-dioxaborolan-2-yl)-benzamide (intermediate 14) (103 mg, 0.25 mmol) and commercially available 5-bromo-4-methyl-pyrimidine (56.2 mg, 325 μmol).

Example 42

*N*-tert-Butyl-3-(4-tert-butyl-pyrimidin-5-yl)-5-(4-chlorophenyl)-benzamide

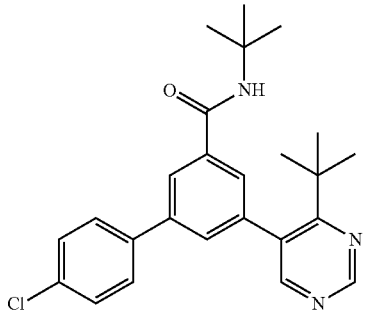 [SMILES: CC(C)(C)NC(=O)c1cc(-c2ccc(Cl)cc2)cc(-c2cncnc2C(C)(C)C)c1]

The title compound, white foam (70 mg, 56%), MS (ISP) m/z=422.4 [(M+H)⁺], mp 108° C., was prepared in accordance with the general method of intermediate 1, step A, from 3-(4-tert-butyl-pyrimidin-5-yl)-5-(4-chlorophenyl)-benzoic acid (intermediate 12) (110 mg, 0.30 mmol) and commercially available 2-methylpropan-2-amine (26.3 mg, 0.36 mmol).

Example 43

3-(4-Chlorophenyl)-*N*-(1-hydroxy-2-methylpropan-2-yl)-5-(4-propan-2-yl-pyrimidin-5-yl)-benzamide

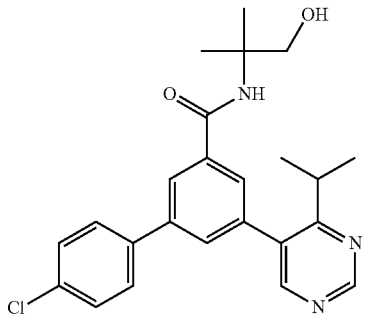 [SMILES: CC(C)c1ncncc1-c1cc(C(=O)NC(C)(C)CO)cc(-c2ccc(Cl)cc2)c1]

The title compound, white foam (70 mg, 66%), MS (ISP) m/z=424.3 [(M+H)⁺], mp 86° C., was prepared in accordance with the general method of example 1 from N-(1-hydroxy-2-methyl-propan-2-yl)-3-iodo-5-(4-propan-2-yl-pyrimidin-5-yl)-benzamide (intermediate 13) (110 mg, 0.25 mmol) and commercially available (4-chlorophenyl)-boronic acid (50.8 mg, 325 μmol).

Example 44

3-(4-Fluorophenyl)-N-(1-hydroxy-2-methylpropan-2yl)-5-(4-propan-2-yl-pyrimidin-5-yl)-benzamide

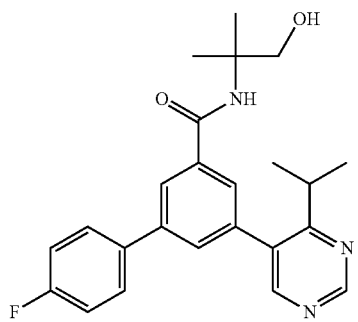 [SMILES: CC(C)c1ncncc1-c1cc(C(=O)NC(C)(C)CO)cc(-c2ccc(F)cc2)c1]

The title compound, white foam (95 mg, 93%), MS (ISP) m/z=408.3 [(M+H)⁺], mp 63° C., was prepared in accordance with the general method of example 1 from N-(1-hydroxy-2-methyl-propan-2-yl)-3-iodo-5-(4-propan-2-yl-pyrimidin-5-yl)-benzamide (intermediate 13) (110 mg, 0.25 mmol) and commercially available (4-fluorophenyl)-boronic acid (45.5 mg, 325 μmol).

Example 45

N-(1-Hydroxy-2-methylpropan-2-yl)-3-(4-propan-2-yl-pyrimidin-5-yl)-5-[4-(trifluoromethyl)-phenyl]-benzamide

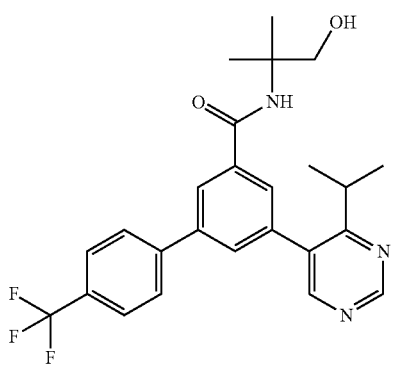 [SMILES: CC(C)c1ncncc1-c1cc(C(=O)NC(C)(C)CO)cc(-c2ccc(C(F)(F)F)cc2)c1]

The title compound, white foam (102 mg, 89%), MS (ISP) m/z=458.4 [(M+H)⁺], mp 80° C., was prepared in accordance with the general method of example 1 from N-(1-hydroxy-2-methyl-propan-2-yl)-3-iodo-5-(4-propan-2-yl-pyrimidin-5-yl)-benzamide (intermediate 13) (110 mg, 0.25 mmol) and commercially available (4-trifluoromethylphenyl)-boronic acid (61.7 mg, 325 μmol).

N-tert-Butyl-3-(4-ethyl-pyrimidin-5-yl)-5-[4-(trifluoromethyl)-phenyl]-benzamide

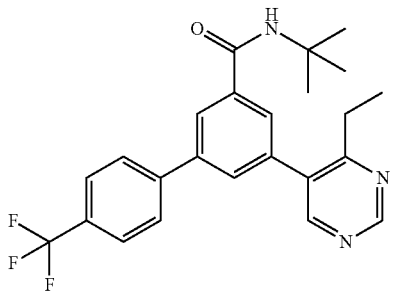 [SMILES: CCc1ncncc1-c1cc(C(=O)NC(C)(C)C)cc(-c2ccc(C(F)(F)F)cc2)c1]

Example 46

The title compound, off-white semisolid (79 mg, 74%), MS (ISP) m/z=428.4 [(M+H)⁺], was prepared in accordance with the general method of example 1 from N-tert-butyl-3-(4,4,5,5-tetramethyl-1,3,2-dioxaborolan-2-yl)-5-[4-(trifluoromethyl)-phenyl]-benzamide (intermediate 15) (112 mg, 0.25 mmol) and commercially available 5-bromo-4-ethyl-pyrimidine (60.8 mg, 325 μmol).

Example 47

N-tert-Butyl-3-(3,4-difluorophenyl)-5-(4-ethyl-pyrimidin-5-yl)-benzamide

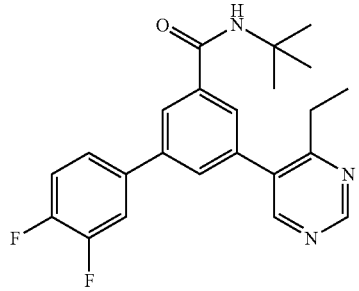 [SMILES: CCc1ncncc1-c1cc(C(=O)NC(C)(C)C)cc(-c2ccc(F)c(F)c2)c1]

The title compound, off-white semisolid (81 mg, 82%), MS (ISP) m/z=396.3 [(M+H)⁺], was prepared in accordance with the general method of example 1 from N-tert-butyl-3-(3,4-difluorophenyl)-5-(4,4,5,5-tetramethyl-1,3,2-dioxaborolan-2-yl)-benzamide (intermediate 16) (104 mg, 0.25 mmol) and commercially available 5-bromo-4-ethyl-pyrimidine (60.8 mg, 325 μmol).

Example 48

N-tert-Butyl-3-(4-tert-butyl-primidin-5-yl)-5-(3,4-difluorophenyl)-benzamide

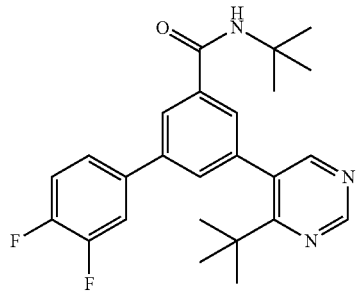 [SMILES: CC(C)(C)NC(=O)c1cc(-c2ccc(F)c(F)c2)cc(-c2cncnc2C(C)(C)C)c1]

The title compound, white foam (43 mg, 41%), MS (ISP) m/z=424.3 [(M+H)⁺], mp 99° C., was prepared in accordance with the general method of example 1 from N-tert-butyl-3-(3,4-difluorophenyl)-5-(4,4,5,5-tetramethyl-1,3,2-dioxaborolan-2-yl)-benzamide (intermediate 16) (104 mg, 0.25 mmol) and commercially available 5-bromo-4-(tert-butyl)-pyrimidine (69.9 mg, 325 μmol).

Example 49

N-tert-Butyl-3-(4-tert-butyl-pyrimidin-5-yl)-5-[4-(trifluoromethyl)-phenyl]-benzamide

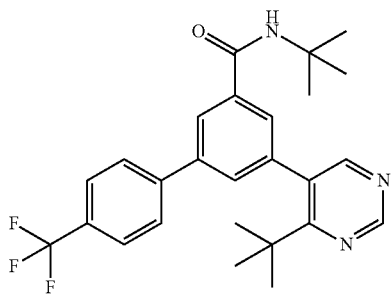 [SMILES: CC(C)(C)NC(=O)c1cc(-c2ccc(C(F)(F)F)cc2)cc(-c2cncnc2C(C)(C)C)c1]

The title compound, off-white foam (49 mg, 43%), MS (ISP) m/z=456.4 [(M+H)⁺], mp 91° C., was prepared in accordance with the general method of example 1 from N-tert-butyl-3-(4,4,5,5-tetramethyl-1,3,2-dioxaborolan-2-yl)-5-[4-(trifluoromethyl)-phenyl]-benzamide (intermediate 15) (112 mg, 0.25 mmol) and commercially available 5-bromo-4-(tert-butyl)-pyrimidine (69.9 mg, 325 μmol).

Example 50

N-tert-Butyl-3-(4-ethyl-pyrimidin-5-yl)-5-(4-fluorophenyl)-benzamide

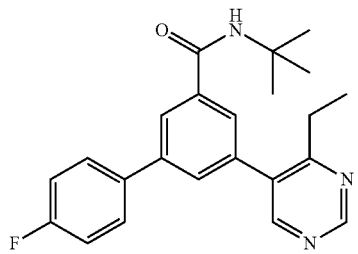 [SMILES: CCc1ncncc1-c1cc(C(=O)NC(C)(C)C)cc(-c2ccc(F)cc2)c1]

The title compound, light yellow semisolid (71 mg, 75%), MS (ISP) m/z=378.3 [(M+H)⁺], was prepared in accordance with the general method of example 1 from N-tert-butyl-3-(4-fluorophenyl)-5-(4,4,5,5-tetramethyl-1,3,2-dioxaborolan-2-yl)-benzamide (intermediate 17) (99.3 mg, 0.25 mmol) and commercially available 5-bromo-4-ethyl-pyrimidine (60.8 mg, 325 μmol).

Example 51

N-tert-Butyl-3-(4-tert-butyl-pyrimidin-5-yl)-5-(4-fluorophenyl)-benziimide

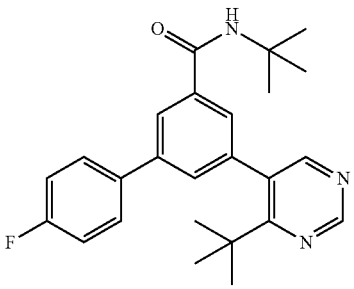 [SMILES: CC(C)(C)NC(=O)c1cc(-c2ccc(F)cc2)cc(-c2cncnc2C(C)(C)C)c1]

The title compound, white solid (70 mg, 69%), MS (ISP) m/z=406.3 [(M+H)⁺], mp 102° C., was prepared in accordance with the general method of example 1 from N-tert-butyl-3-(4-fluorophenyl)-5-(4,4,5,5-tetramethyl-1,3,2-dioxaborolan-2-yl)-benzamide (intermediate 17) (99.3 mg, 0.25 mmol) and commercially available 5-bromo-4-(tert-butyl)-pyrimidine (69.9 mg, 325 μmol).

Example 52

N-tert-Butyl-3-(4-tert-butyl-pyridin-3-yl)-5-(4-fluorophenyl)-benzamide

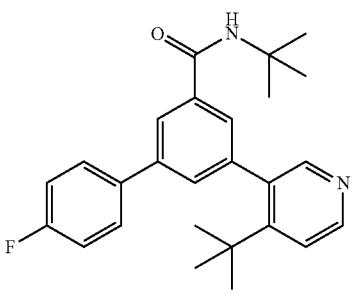 [SMILES: CC(C)(C)NC(=O)c1cc(-c2ccc(F)cc2)cc(-c2cnccc2C(C)(C)C)c1]

The title compound, light yellow oil (60 mg, 59%), MS (ISP) m/z=405.3 [(M+H)⁺], was prepared in accordance with the general method of example 1 from N-tert-butyl-3-(4-fluorophenyl)-5-(4,4,5,5-tetramethyl-1,3,2-dioxaborolan-2-yl)-benzamide (intermediate 17) (99.3 mg, 0.25 mmol) and commercially available 3-bromo-4-(tert-butyl)-pyridine [CAS-No. 90731-98-9] (69.6 mg, 325 μmol).

Example 53

N-tert-Butyl-3-(4-tert-butylpyridin-3-yl)-5-(4-chlorophenyl)-benzamide

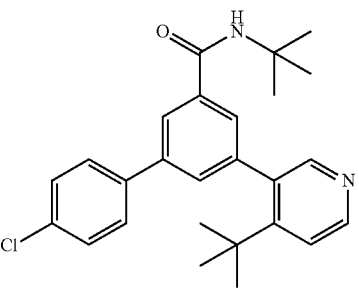 [SMILES: CC(C)(C)NC(=O)c1cc(-c2ccc(Cl)cc2)cc(-c2cnccc2C(C)(C)C)c1]

The title compound, light brown foam (50 mg, 48%), MS (ISP) m/z=421.3 [(M+H)+], mp 63.5° C., was prepared in accordance with the general method of example 1 from N-tert-butyl-3-(4-chlorophenyl)-5-(4,4,5,5-tetramethyl-1,3, 2-dioxaborolan-2-yl)-benzamide (intermediate 14) (103 mg, 0.25 mmol) and commercially available 3-bromo-4-(tert-butyl)-pyridine [CAS-No. 90731-98-9] (69.6 mg, 325 µmol).

We claim:
1. A compound of formula I

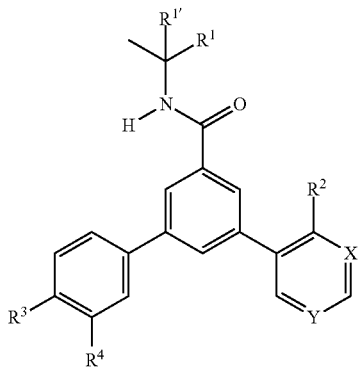

wherein
R$^{1'}$ is methyl;
R$^1$ is methyl, ethyl, CF$_3$, CH$_2$OH, cyclopropyl or cyano, or
R$^{1'}$ and R$^1$ may form together a 1,1-dioxo-tetrahydro-thiophen-3-yl ring;
R$^2$ is hydrogen, methyl, ethyl, isopropyl, tert-butyl or cyclopropyl;
R$^3$ is Cl, F, CF$_3$, cyano, methyl, methoxy or cyclopropyl;
R$^4$ is hydrogen, methyl or F;
X is N or CH;
Y is N or CH;
with the proviso that X and Y are not simultaneously CH;
or a pharmaceutically acceptable salt or acid addition salt, a racemic mixture, or a corresponding enantiomer or mixture of enantiomers and/or optical isomer and/or stereoisomer thereof.

2. The compound of formula IA according to claim 1

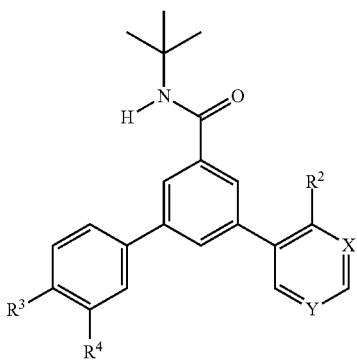

wherein
R$^2$ is hydrogen, methyl, ethyl, isopropyl, tert-butyl or cyclopropyl;
R$^3$ is Cl, F, CF$_3$, cyano, methyl, methoxy or cyclopropyl;
R$^4$ is hydrogen, methyl or F;
X is N or CH;
Y is N or CH;
with the proviso that X and Y are not simultaneously CH;
or a pharmaceutically acceptable salt or acid addition salt, a racemic mixture, or its corresponding enantiomer or mixture of enantiomers and/or optical isomer and/or stereoisomer thereof.

3. The compound of formula IA according to claim 2, which compound is:
N-tert-Butyl-3-(4-chlorophenyl)-5-(4-methylpyridin-3-yl)-benzamide;
N-tert-Butyl-3-(4-chlorophenyl)-5-pyridin-3-ylbenzamide;
N-tert-Butyl-3-(4-chlorophenyl)-5-(4-propan-2-ylpyridin-3-yl)-benzamide;
N-tert-Butyl-3-(4-chlorophenyl)-5-pyrimidin-5-ylbenzamide;
N-tert-Butyl-3-(4-chlorophenyl)-5-(4-propan-2-ylpyrimidin-5-yl)-benzamide;
N-tert-Butyl-3-(4-chlorophenyl)-5-(2-propan-2-ylpyridin-3-yl)-benzamide;
N-tert-Butyl-3-(4-fluorophenyl)-5-(4-propan-2-ylpyrimidin-5-yl)-benzamide;
N-tert-Butyl-3-(4-fluorophenyl)-5-(4-methylpyridin-3-yl)-benzamide;
N-tert-Butyl-3-(4-fluorophenyl)-5-(2-methylpyridin-3-yl)-benzamide;
N-tert-Butyl-3-(4-methylphenyl)-5-(4-propan-2-ylpyrimidin-5-yl)-benzamide;
N-tert-Butyl-3-(3,4-difluorophenyl)-5-(4-propan-2-ylpyrimidin-5-yl)-benzamide;
N-tert-Butyl-3-(4-cyclopropylphenyl)-5-(4-propan-2-ylpyrimidin-5-yl)-benzamide;
N-tert-Butyl-3-(4-propan-2-ylpyrimidin-5-yl)-5-[4-(trifluoromethyl)-phenyl]-benzamide;
N-tert-Butyl-3-(4-fluoro-3-methylphenyl)-5-(4-propan-2-ylpyrimidin-5-yl)-benzamide;
N-tert-Butyl-3-(3-fluoro-4-methylphenyl)-5-(4-propan-2-ylpyrimidin-5-yl)-benzamide;
N-tert-Butyl-3-(4-chloro-3-fluorophenyl)-5-(4-propan-2-ylpyrimidin-5-yl)-benzamide;
N-tert-Butyl-3-(4-cyanophenyl)-5-(4-propan-2-ylpyrimidin-5-yl)-benzamide;
N-tert-Butyl-3-(4-methoxyphenyl)-5-(4-propan-2-ylpyrimidin-5-yl)-benzamide;
N-tert-Butyl-3-(4-chlorophenyl)-5-(4-cyclopropyl-pyrimidin-5-yl)-benzamide;
N-tert-Butyl-3-(4-chlorophenyl)-5-(4-ethyl-pyrimidin-5-yl)-benzamide;
N-tert-Butyl-3-(4-chlorophenyl)-5-(4-methyl-pyrimidin-5-yl)-benzamide; or,
N-tert-Butyl-3-(4-tert-butyl-pyrimidin-5-yl)-5-(4-chlorophenyl)-benzamide.

4. The compound of formula IA according to claim 2, which compound is:
N-tert-butyl-3-(4-ethylpyrimidin-5-yl)-5-[4-(trifluoromethyl)phenyl]benzamide;
N-tert-butyl-3-(3,4-difluorophenyl)-5-(4-ethylpyrimidin-5-yl)benzamide;
N-tert-butyl-3-(4-tert-butylpyrimidin-5-yl)-5-(3,4-difluorophenyl)benzamide;
N-tert-butyl-3-(4-tert-butylpyrimidin-5-yl)-5-[4-(trifluoromethyl)phenyl]benzamide;
N-tert-butyl-3-(4-ethylpyrimidin-5-yl)-5-(4-fluorophenyl)benzamide;

N-tert-butyl-3-(4-tert-butylpyrimidin-5-yl)-5-(4-fluorophenyl)benzamide;

N-tert-butyl-3-(4-tert-butylpyridin-3-yl)-5-(4-fluorophenyl)benzamide; or,

N-tert-butyl-3-(4-tert-butylpyridin-3-yl)-5-(4-chlorophenyl)benzamide.

5. The compound of formula IB according to claim 1

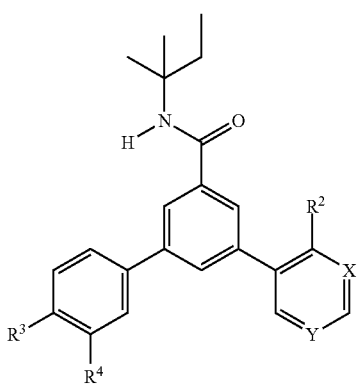

IB wherein

R² is hydrogen, methyl, ethyl, isopropyl, tert-butyl or cyclopropyl;

R³ is Cl, F, CF₃, cyano, methyl, methoxy or cyclopropyl;

R⁴ is hydrogen, methyl or F;

X is N or CH;

Y is N or CH;

with the proviso that X and Y are not simultaneously CH;

or a pharmaceutically acceptable salt or acid addition salt, a racemic mixture, or its corresponding enantiomer, or mixture of enantiomers, and/or optical isomer and/or stereoisomer thereof.

6. The compound of formula IB according to claim 4, wherein the compound is:

N-(2-Methylbutan-2-yl)-3-(4-methylphenyl)-5-pyridin-3-ylbenzamide;

N-(2-Methylbutan-2-yl)-3-(4-methylphenyl)-5-pyrimidin-5-ylbenzamide;

N-(2-Methylbutan-2-yl)-3-(4-methylphenyl)-5-(4-propan-2-ylpyrimidin-5-yl)-benzamide;

N-(2-Methylbutan-2-yl)-3-(4-methylphenyl)-5-(4-methylpyridin-3-yl)-benzamide;

N-(2-Methylbutan-2-yl)-3-(4-methylphenyl)-5-(2-methylpyridin-3-yl)-benzamide;

N-(2-Methylbutan-2-yl)-3-(4-methylphenyl)-5-(4-propan-2-ylpyridin-3-yl)-benzamide; or, N-(2-Methylbutan-2-yl)-3-(4-methylphenyl)-5-(2-propan-2-ylpyridin-3-yl)-benzamide.

7. The compound of formula IC according to claim 1

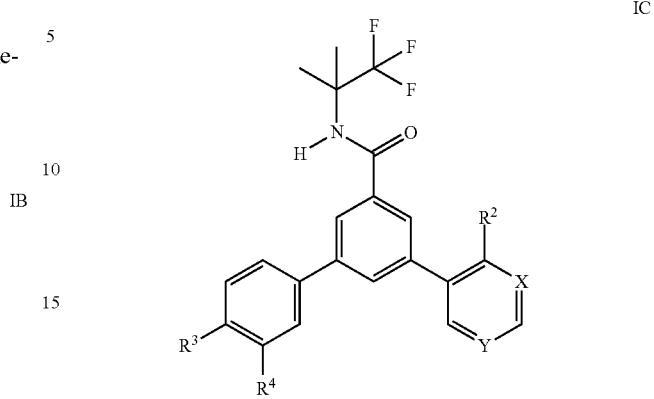

IC wherein

R² is hydrogen, methyl, ethyl, isopropyl, tert-butyl or cyclopropyl;

R³ is Cl, F, CF₃, cyano, methyl, methoxy or cyclopropyl;

R⁴ is hydrogen, methyl or F;

X is N or CH;

Y is N or CH;

with the proviso that X and Y are not simultaneously CH;

or a pharmaceutically acceptable salt or acid addition salt, a racemic mixture, or its corresponding enantiomer, or mixture of enantiomers, and/or optical isomer and/or stereoisomer thereof.

8. The compound of formula IC according to claim 6, wherein the compound is:

3-(4-Chlorophenyl)-5-(4-propan-2-ylpyrimidin-5-yl)-N-(1,1,1-trifluoro-2-methylpropan-2-yl)-benzamide; or, 3-(4-Chlorophenyl)-5-(2-methylpyridin-3-yl)-N-(1,1,1-trifluoro-2-methylpropan-2-yl)-benzamide.

9. The compound of formula ID according to claim 1

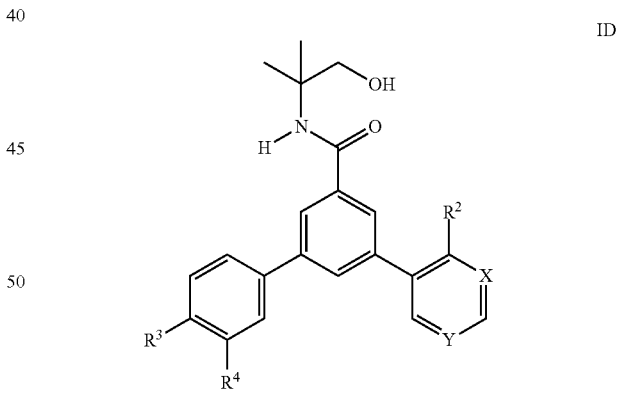

ID wherein

R² is hydrogen, methyl, ethyl, isopropyl, tert-butyl or cyclopropyl;

R³ is Cl, F, CF₃, cyano, methyl, methoxy or cyclopropyl;

R⁴ is hydrogen, methyl or F;

X is N or CH;

Y is N or CH;

with the proviso that X and Y are not simultaneously CH;

or a pharmaceutically acceptable salt or acid addition salt, a racemic mixture, or its corresponding enantiomer, or mixture of enantiomers, and/or optical isomer and/or stereoisomer thereof.

10. The compound of formula ID according to claim 8, wherein the compound is:
- 3-(4-Chlorophenyl)-N-(1-hydroxy-2-methylpropan-2-yl)-5-(4-propan-2-yl-pyrimidin-5-yl)-benzamide;
- 3-(4-Fluorophenyl)-N-(1-hydroxy-2-methylpropan-2-yl)-5-(4-propan-2-yl-pyrimidin-5-yl)-benzamide; or,
- N-(1-Hydroxy-2-methylpropan-2-yl)-3-(4-propan-2-yl-pyrimidin-5-yl)-5-[4-(trifluoromethyl)-phenyl]-benzamide.

11. The compound of formula IE according to claim 1,

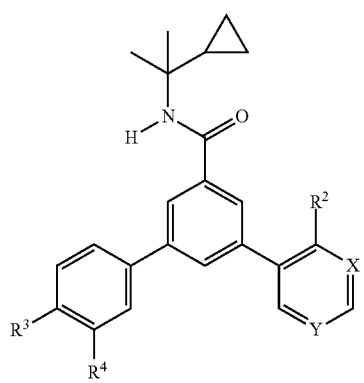

IE wherein
- $R^2$ is hydrogen, methyl, ethyl, isopropyl, tert-butyl or cyclopropyl;
- $R^3$ is Cl, F, $CF_3$, cyano, methyl, methoxy or cyclopropyl;
- $R^4$ is hydrogen, methyl or F;
- X is N or CH;
- Y is N or CH;
  - with the proviso that X and Y are not simultaneously CH;
- or a pharmaceutically acceptable salt or acid addition salt, a racemic mixture, or its corresponding enantiomer, or mixture of enantiomers, and/or optical isomer and/or stereoisomer thereof.

12. The compound of formula IE according to claim 10, which compound is:
- 3-(4-Chlorophenyl)-N-(2-cyclopropylpropan-2-yl)-5-(4-propan-2-ylpyrimidin-5-yl)-benzamide;
- 3-(4-Chlorophenyl)-N-(2-cyclopropylpropan-2-yl)-5-(2-methylpyridin-3-yl)-benzamide;
- N-(2-Cyclopropylpropan-2-yl)-3-(4-fluorophenyl)-5-(4-propan-2-ylpyrimidin-5-yl)-benzamide; or,
- N-(2-Cyclopropylpropan-2-yl)-3-(4-fluorophenyl)-5-(4-methylpyridin-3-yl)-benzamide.

13. The compound of formula IF according to claim 1,

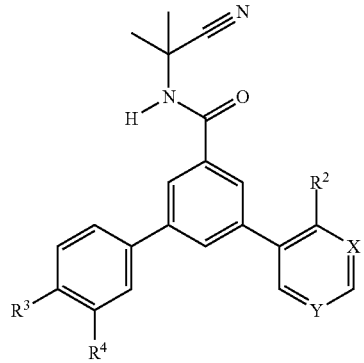

IF wherein
- $R^2$ is hydrogen, methyl, ethyl, isopropyl, tert-butyl or cyclopropyl;
- $R^3$ is Cl, F, $CF_3$, cyano, methyl, methoxy or cyclopropyl;
- $R^4$ is hydrogen, methyl or F;
- X is N or CH;
- Y is N or CH;
  - with the proviso that X and Y are not simultaneously CH;
- or a pharmaceutically acceptable salt or acid addition salt, a racemic mixture, or its corresponding enantiomer, or mixture of enantiomers, and/or optical isomer and/or stereoisomer thereof.

14. The compound of formula IF according to claim 12, which compound is:
- N-(2-Cyanopropan-2-yl)-3-(3-fluoro-4-methylphenyl)-5-(4-propan-2-yl-pyrimidin-5-yl)-benzamide;
- N-(2-Cyanopropan-2-yl)-3-(4-fluoro-3-methylphenyl)-5-(4-propan-2-yl-pyrimidin-5-yl)-benzamide;
- N-(2-Cyanopropan-2-yl)-3-(4-fluorophenyl)-5-(4-propan-2-yl-pyrimidin-5-yl)-benzamide;
- N-(2-Cyanopropan-2-yl)-3-(4-propan-2-yl-pyrimidin-5-yl)-5-[4-(trifluoromethyl)-phenyl]-benzamide; or,
- 3-(4-Chlorophenyl)-N-(2-cyanopropan-2-yl)-5-(4-propan-2-yl-pyrimidin-5-yl)-benzamide.

15. The compound of formula IG according to claim 1,

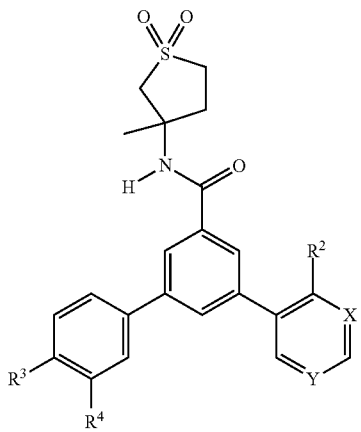

IG wherein
- $R^2$ is hydrogen, methyl, ethyl, isopropyl, tert-butyl or cyclopropyl;
- $R^3$ is Cl, F, $CF_3$, cyano, methyl, methoxy or cyclopropyl;
- $R^4$ is hydrogen, methyl or F;
- X is N or CH;
- Y is N or CH; with the proviso that X and Y are not simultaneously CH;
- or a pharmaceutically acceptable salt or acid addition salt, a racemic mixture, or its corresponding enantiomer, or mixture of enantiomers, and/or optical isomer and/or stereoisomer thereof.

16. The compound of formula IG according to claim 14, which compound is:
- (RS)-3-(4-Chlorophenyl)-N-(3-methyl-1,1-dioxothiolan-3-yl)-5-(4-propan-2-ylpyrimidin-5-yl)-benzamide; or,
- (RS)-3-(4-Chlorophenyl)-N-(3-methyl-1,1-dioxothiolan-3-yl)-5-(2-methyl-pyridin-3-yl)-benzamide.

17. A process for the manufacture of a compound of formula I as defined claim 1, which process comprises
a) reacting a compound of formula II

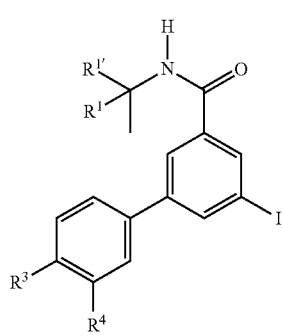

II with a compound of formula III

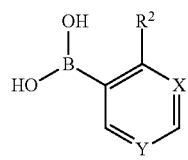

III to form compound of formula I

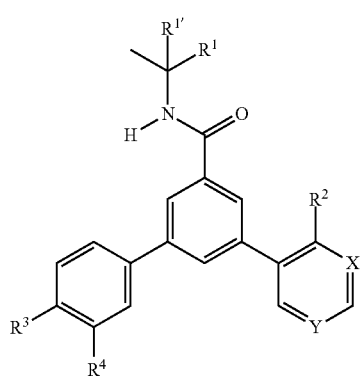

I wherein the substituents are as described in claim 1, or, if desired, converting the compounds obtained into pharmaceutically acceptable acid addition salts.

18. A process for the manufacture of a compound of formula I as defined claim 1, which process comprises reacting a compound of formula IV

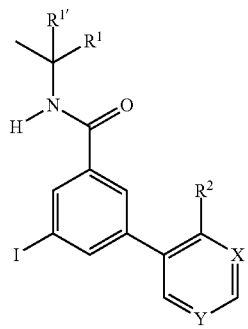

IV with a compound of formula V

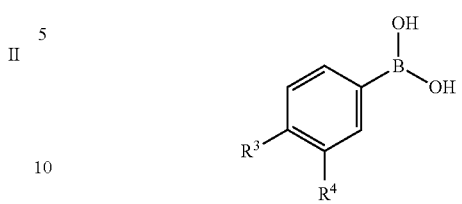

V to form a compound of formula I

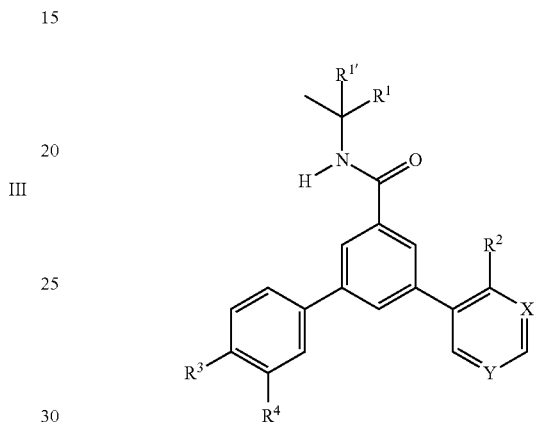

I wherein the substituents are described in claim 1, or, if desired, converting the compounds obtained into pharmaceutically acceptable acid addition salts.

19. A process for the manufacture of a compound of formula I as defined claim 1, which process comprises reacting a compound of formula XVII

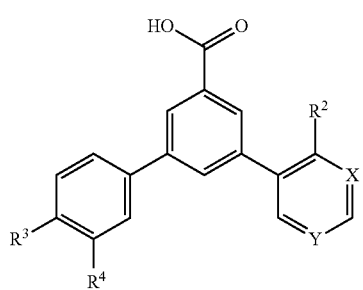

XVII with a compound of formula VII

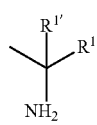

VII to a compound of formula I

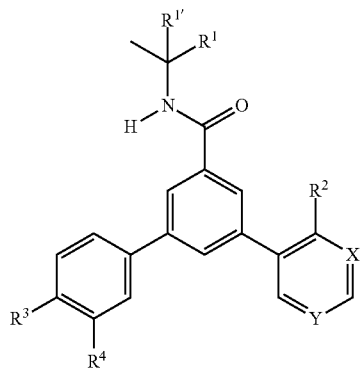

wherein the substituents are described in claim 1, or if desired, converting the compounds obtained into pharmaceutically acceptable acid addition salts.

20. A process for the manufacture of a compound of formula I as defined claim 1, which process comprises reacting a compound of formula XVIII

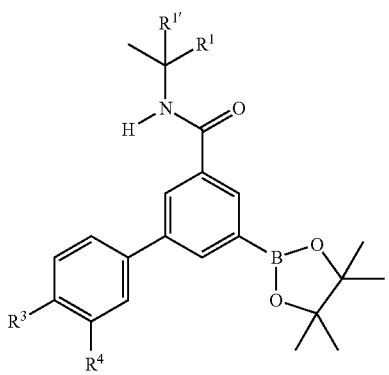

with a compound of formula XVI

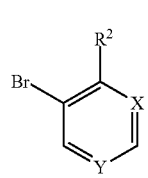

to a compound of formula I

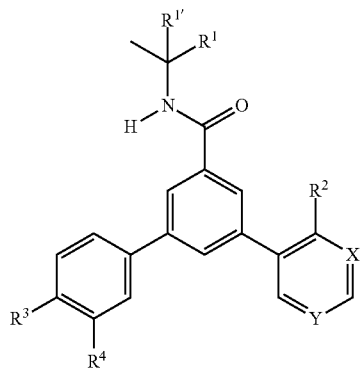

wherein the substituents are described in claim 1, or if desired, converting the compounds obtained into pharmaceutically acceptable acid addition salts.

21. A pharmaceutical composition comprising a compound of formula I according to claim 1 and at least one pharmaceutically acceptable excipient, carrier or diluent.

22. A method for the treatment of schizophrenia, bipolar disorder, obsessive-compulsive disorder or autism spectrum disorder which method comprises administering a therapeutically effective amount of a compound of formula I according to claim 1 to a patient in need thereof.

* * * * *